US010048420B2

(12) United States Patent
Adlem et al.

(10) Patent No.: US 10,048,420 B2
(45) Date of Patent: Aug. 14, 2018

(54) REACTIVE MESOGENS

(71) Applicant: MERCK PATENT GMBH, Darmstadt (DE)

(72) Inventors: Kevin Adlem, Bournemouth (GB);
Owain Llyr Parri, Ringwood (GB);
Graham Smith, Chilworth (GB);
Patricia Eileen Saxton, Romsey (GB);
Mariam Namutebi, Southampton (GB);
Vicki Cook, Southampton (GB);
Joseph Sargent, Southampton (GB)

(73) Assignee: MERCK PATENT GMBH, Darmstadt (DE)

( * ) Notice: Subject to any disclaimer, the term of this patent is extended or adjusted under 35 U.S.C. 154(b) by 140 days.

(21) Appl. No.: 14/654,079

(22) PCT Filed: Nov. 18, 2013

(86) PCT No.: PCT/EP2013/003462
§ 371 (c)(1),
(2) Date: Jun. 19, 2015

(87) PCT Pub. No.: WO2014/094949
PCT Pub. Date: Jun. 26, 2014

(65) Prior Publication Data
US 2015/0323722 A1 Nov. 12, 2015

(30) Foreign Application Priority Data

Dec. 21, 2012 (EP) .................................... 12008583

(51) Int. Cl.
| | | |
|---|---|---|
| G02B 5/30 | (2006.01) | |
| G02B 1/08 | (2006.01) | |
| C07C 255/55 | (2006.01) | |
| C07C 255/54 | (2006.01) | |
| C07C 321/14 | (2006.01) | |
| C08G 75/045 | (2016.01) | |
| C08G 75/04 | (2016.01) | |
| C09K 19/38 | (2006.01) | |
| C09K 19/04 | (2006.01) | |
| C09K 19/12 | (2006.01) | |
| C08F 22/10 | (2006.01) | |
| C08F 22/20 | (2006.01) | |

(52) U.S. Cl.
CPC .......... *G02B 5/3083* (2013.01); *C07C 255/54* (2013.01); *C07C 255/55* (2013.01); *C07C 321/14* (2013.01); *C08F 22/10* (2013.01); *C08F 22/20* (2013.01); *C08G 75/045* (2013.01); *C09K 19/04* (2013.01); *C09K 19/12* (2013.01); *C09K 19/3842* (2013.01); *C09K 19/3852* (2013.01); *G02B 1/08* (2013.01); *C09K 2019/0448* (2013.01); *C09K 2019/123* (2013.01)

(58) Field of Classification Search
CPC .... C07C 255/55; C07C 255/54; C07C 321/14
See application file for complete search history.

(56) References Cited

U.S. PATENT DOCUMENTS

| | | | | |
|---|---|---|---|---|
| 5,332,522 | A * | 7/1994 | Chen ..................... | C08F 220/30 252/299.01 |
| 5,518,652 | A | 5/1996 | Parri et al. | |
| 5,720,900 | A * | 2/1998 | Parri ..................... | C08F 220/30 252/299.01 |
| 5,723,066 | A | 3/1998 | Coates et al. | |
| 5,746,938 | A | 5/1998 | Coates et al. | |
| 5,871,665 | A | 2/1999 | Coates et al. | |
| 6,042,745 | A | 3/2000 | Coates et al. | |
| 6,187,222 | B1 | 2/2001 | Coates et al. | |
| 6,565,769 | B2 | 5/2003 | Coates et al. | |
| 6,582,626 | B2 | 6/2003 | Hasebe et al. | |
| 6,596,193 | B2 | 7/2003 | Coates et al. | |
| 6,599,590 | B2 | 7/2003 | Haseba et al. | |
| 6,682,661 | B2 | 1/2004 | Coates et al. | |
| 7,098,365 | B2 | 8/2006 | Yoshida et al. | |
| 7,432,228 | B2 | 10/2008 | Yoshida et al. | |
| 7,524,436 | B2 * | 4/2009 | Harding ............. | C09K 19/2007 252/299.01 |
| 2001/0016238 | A1 | 8/2001 | Coates et al. | |
| 2002/0015805 | A1 | 2/2002 | Haseba et al. | |
| 2002/0060310 | A1 | 5/2002 | Hasebe et al. | |
| 2002/0158227 | A1 | 10/2002 | Coates et al. | |
| 2003/0064173 | A1 | 4/2003 | Coates et al. | |
| 2005/0014651 | A1 | 1/2005 | Yoshida et al. | |
| 2006/0148650 | A1 | 7/2006 | Yoshida et al. | |

(Continued)

FOREIGN PATENT DOCUMENTS

| | | |
|---|---|---|
| EP | 0648827 B1 | 12/1999 |
| EP | 1158037 A1 | 11/2001 |

(Continued)

OTHER PUBLICATIONS

Machine translation of JP 07-101900 A1, retrieved Jan. 2017.*
Machine translation of JP 2007-169362 A, retrieved Jun. 2017.*
International Search report dated Feb. 4, 2014 issued in corresponding PCT/EP2013/003462 application (pp. 1-3).
Office Action in corresponding Japanese Application No. 2015-548249 dated Oct. 26, 2017.
Zhang; Synthesis of Novel Liquid Crystal Poly(meth)acrylates containing Siloxane Spacer and Terphenylene Mesogenic Unit, Chinese Journal of Polymer Science, 2000, 18(2), pp. 101-107.
Office Action in corresponding EP Application No. 13791938.7 dated Oct. 26, 2017.

(Continued)

*Primary Examiner* — Nicole M Buie-Hatcher
(74) *Attorney, Agent, or Firm* — Millen, White, Zelano and Branigan, P.C.

(57) ABSTRACT

The invention relates to reactive mesogens (RMs) comprising a terphenyl group, to mixtures and formulations comprising them, to polymers obtained form such RMs and RM mixtures, and the use of the RMs, RM mixtures and polymers in optical or electrooptical components or devices, like optical retardation films for liquid crystal displays (LCDs).

12 Claims, 1 Drawing Sheet

(56) References Cited

U.S. PATENT DOCUMENTS

| | | |
|---|---|---|
| 2006/0172090 A1 | 8/2006 | Syundo |
| 2007/0018136 A1 | 1/2007 | Goto et al. |
| 2008/0099726 A1 | 5/2008 | Kubo |
| 2011/0108793 A1* | 5/2011 | Wessels ................ B82Y 10/00 257/4 |

FOREIGN PATENT DOCUMENTS

| | | | | |
|---|---|---|---|---|
| EP | 1205467 A | | 5/2002 | |
| EP | 1256617 A1 | | 11/2002 | |
| GB | 2280445 A | * | 2/1995 | ............ C08F 220/30 |
| JP | 07101900 A | * | 4/1995 | |
| JP | 2001-220583 A | | 8/2001 | |
| JP | 2004-123829 A | | 4/2004 | |
| JP | 2007169362 A | * | 7/2007 | |
| JP | 2007169363 A | * | 7/2007 | |
| JP | 04-029960 B2 | | 1/2008 | |
| JP | 2008-133470 A | | 6/2008 | |
| JP | 48-34907 B2 | | 12/2011 | |
| WO | 9322397 A1 | | 11/1993 | |

OTHER PUBLICATIONS

Yamada; Investigation on Monomers for a New Polymer-LC Dispersed Structure; Molecular Crystals and Liquid Crystals 332 (1):447-454—Aug. 1999 (D11).

Office Action in corresponding JP Application No. 2015-548249 dated Feb. 23, 2018.

Oriol, L. et al., Synthesis and characterization of reactive liquid crystals and polymers based on terphenyl derivatives, Polymer, 2001 (2001) 42(7), 2737-2744.

Sanchez, C. et al., Polarized photoluminescence and order parameters of "in situ" photopolymerized liquid crystal films, Journal of Applied Physics, 2000, (2000), 87(1), 274-279.

* cited by examiner

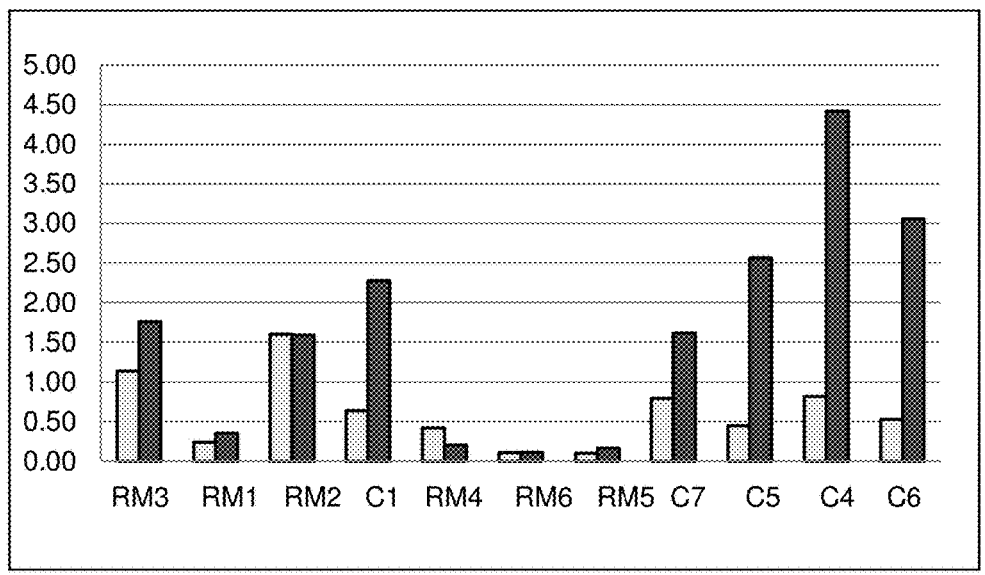

REACTIVE MESOGENS

FIELD OF THE INVENTION

The invention relates to reactive mesogens (RMs) comprising a terphenyl group, to mixtures and formulations comprising them, to polymers obtained form such RMs and RM mixtures, and the use of the RMs, RM mixtures and polymers in optical or electrooptical components or devices, like optical retardation films for liquid crystal displays (LCDs).

BACKGROUND AND PRIOR ART

Reactive mesogens (RMs), mixtures or formulations comprising them, and polymers obtained thereof, can be used to make optical components, like compensation, retardation or polarisation films, or lenses. These optical components can be used in optical or electrooptical devices like LC displays. Usually the RMs or RM mixtures are polymerised through the process of in-situ polymerisation.

The manufacture of RM film products with high birefringence is of high importance for manufacturing optical components of modern display devices like LCDs. Increasing the birefringence of the RM whilst keeping them polymerisable and with good physical properties is possible, but requires to incorporate specific chemical groups, like for example tolane groups, into the compounds. These tolane groups are relatively reactive and are generally unsuited to light exposure, making them difficult to utilise in many optical applications due to yellowing or other degradation effects.

It is therefore an aim of the present invention to provide improved RMs and RM formulations, which do not have the drawbacks of materials known from prior art. In particular it is an aim to provide RMs and RM formulations that are suitable for preparing polymers by in situ UV photopolymerisation, have a high birefringence, and show high resistance against yellowing after being exposed to UV light. Other aims of the invention are immediately evident to the expert from the following description.

The inventors have of the present invention have found that these aims can be achieved by providing RMs and RM formulations as disclosed and claimed hereinafter.

SUMMARY OF THE INVENTION

The invention relates to compounds of formula I

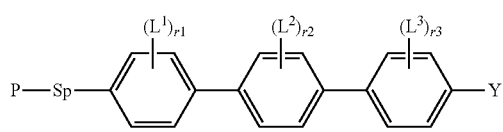

I wherein
P is a polymerisable group,
Sp is a spacer group or a single bond,
$L^1$, $L^2$, $L^3$ are independently of each other P-Sp-, F, Cl, Br, I, —CN, —$NO_2$, —NCO, —NCS, —OCN, —SCN, —C(=O)$NR^{00}R^{000}$, —C(=O)X, —C(=O)$OR^{00}$, —C(=O)$R^0$, —$NR^{00}R^{000}$, —OH, —$SF_5$, optionally substituted silyl, aryl or heteroaryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl,
r1, r2, r3 are independently of each other 0, 1, 2, 3 or 4,
$R^{00}$, $R^{000}$ independently of each other denote H or alkyl with 1 to 12 C-atoms,
Y is CN, F, Cl, $OCF_3$, $OCH_3$ or $CF_3$.

The invention further relates to a mixture, which is hereinafter referred to as "RM mixture", comprising two or more RMs, at least one of which is a compound of formula I.

The invention further relates to a formulation, which is hereinafter referred to as "RM formulation", comprising one or more compounds of formula I or an RM mixture as described above and below, and further comprising one or more solvents and/or additives.

The invention further relates to a polymer obtainable by polymerising a compound of formula I or an RM mixture as described above and below, preferably wherein the RMs are aligned, and preferably at a temperature where the RMs or RM mixture exhibit a liquid crystal phase.

The invention further relates to the use of the compounds of formula I, the RM mixture or the polymer as described above and below in optical, electrooptical or electronic components or devices.

The invention further relates to an optical, electrooptical or electronic device or a component thereof, comprising an RM, RM mixture or polymer as described above and below.

Said components include, without limitation, optical retardation films, polarizers, compensators, beam splitters, reflective films, alignment layers, colour filters, antistatic protection sheets, electromagnetic interference protection sheets, polarization controlled lenses for example for autostereoscopic 3D displays, and IR reflection films for example for window applications.

Said devices include, without limitation, electrooptical displays, especially LC displays, autostereoscopic 3D displays, organic light emitting diodes (OLEDs), optical data storage devices, and windows.

BRIEF DESCRIPTION OF THE DRAWINGS

FIG. 1 shows the comparison ΔE(lab) data of RMs according to prior art and RMs according to the invention in anhydrous DCM.

DEFINITIONS OF TERMS

As used herein, the term "RM mixture" means a mixture comprising two or more RMs, and optionally comprising further materials.

As used herein, the term "RM formulation" means at least one RM or RM mixture, and one or more other materials added to the at least one RM or RM mixture to provide, or to modify, specific properties of the RM formulation and/or of the at least one RM therein. It will be understood that an RM formulation is also a vehicle for carrying the RM to a substrate to enable the forming of layers or structures thereon. Exemplary materials include, but are not limited to, solvents, polymerisation initiators, surfactants and adhesion promoters.

The term "reactive mesogen" (RM) as used herein means a polymerisable mesogenic or liquid crystalline compound, which is preferably a monomeric compound.

The terms "liquid crystal", "mesogen" and "mesogenic compound" as used herein mean a compound that under suitable conditions of temperature, pressure and concentration can exist as a mesophase or in particular as a LC phase.

The term "mesogenic group" as used herein means a group with the ability to induce liquid crystal (LC) phase behaviour. Mesogenic groups, especially those of the non-amphiphilic type, are usually either calamitic or discotic. The compounds comprising mesogenic groups do not necessarily have to exhibit an LC phase themselves. It is also possible that they show LC phase behaviour only in mixtures with other compounds, or when the mesogenic compounds or the mixtures thereof are polymerised. For the sake of simplicity, the term "liquid crystal" is used hereinafter for both mesogenic and LC materials.

The term "calamitic" as used herein means a rod- or board/lath-shaped compound or group. The term "banana-shaped" as used herein means a bent group in which two, usually calamitic, mesogenic groups are linked through a semi-rigid group in such a way as not to be collinear.

The term "discotic" as used herein means a disc- or sheet-shaped compound or group.

A calamitic mesogenic compound is usually comprising a calamitic, i.e. rod- or lath-shaped, mesogenic group consisting of one or more aromatic or alicyclic groups connected to each other directly or via linkage groups, optionally comprising terminal groups attached to the short ends of the rod, and optionally comprising one or more lateral groups attached to the long sides of the rod, wherein these terminal and lateral groups are usually selected e.g. from carbyl or hydrocarbyl groups, polar groups like halogen, nitro, hydroxy, etc., or polymerisable groups.

A discotic mesogenic compound is usually comprising a discotic, i.e. relatively flat disc- or sheet-shaped mesogenic group consisting for example of one or more condensed aromatic or alicyclic groups, like for example triphenylene, and optionally comprising one or more terminal groups that are attached to the mesogenic group and are selected from the terminal and lateral groups mentioned above.

For an overview of terms and definitions in connection with liquid crystals and mesogens see Pure Appl. Chem. 73(5), 888 (2001) and C. Tschierske, G. Pelzl and S. Diele, Angew. Chem. 2004, 116, 6340-6368.

Polymerisable compounds with one polymerisable group are also referred to as "monoreactive" compounds, compounds with two polymerisable groups as "direactive" compounds, and compounds with more than two polymerisable groups as "multireactive" compounds. Compounds without a polymerisable group are also referred to as "non-reactive" compounds.

The term "spacer" or "spacer group" as used herein, also referred to as "Sp" below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless stated otherwise, the term "spacer" or "spacer group" above and below denotes a flexible organic group, which in a polymerisable mesogenic compound ("RM") connects the mesogenic group and the polymerisable group(s).

The term "film" as used herein includes rigid or flexible, self-supporting or free-standing films with mechanical stability, as well as coatings or layers on a supporting substrate or between two substrates. "Thin film" means a film having a thickness in the nanometer or micrometer range, preferably at least 10 nm, very preferably at least 100 nm, and preferably not more than 100 μm, very preferably not more than 10 μm.

The term "hydrocarbyl group" means any monovalent or multivalent organic radical moiety which comprises at least one carbon atom and optionally one or more H atoms, and optionally one or more hetero atoms like for example N, O, S, P, Si, Se, As, Te or Ge. A hydrocarbyl group comprising a chain of 3 or more C atoms may also be linear, branched and/or cyclic, including spiro and/or fused rings.

DETAILED DESCRIPTION

Preferred compounds of formula I are those selected of formula I1

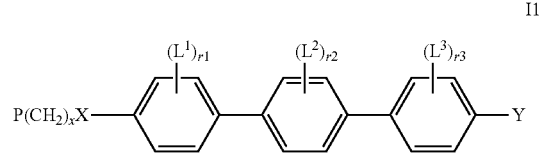

wherein P, Y, $L^1$, $L^2$, $L^3$, r1, r2 and r3 are as defined in formula I, X denotes O, —O—CO—, —CO—O—, —C≡C— or a single bond, and x is an integer from 0 to 12, preferably from 1 to 8, very preferably 3, 4, 5 or 6.

Very preferred are compounds of formula I wherein P is selected from the group consisting of vinyloxy, acrylate, methacrylate, fluoroacrylate, chloroacrylate, oxetane and epoxide groups, and very preferably denotes an acrylate, methacrylate or oxetane group.

Further preferred are compounds of formula I or I1, wherein:
  Y is CN,
  r1=r3=0 and r2=1,
  r1=r3=0 and r2=2,
  r1=0, r2=1 or 2 and r3=1 or 2,
  $L^1$, $L^2$ and $L^3$ denote independently of each other F or $CH_3$, preferably F,
  X is —O— or a single bond,
  X is —C≡C—,
or any combination of the aforementioned.

Preferred compounds of formula I1 are selected of the following formulae

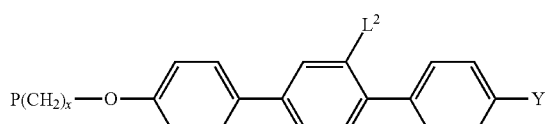

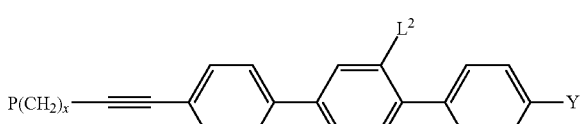

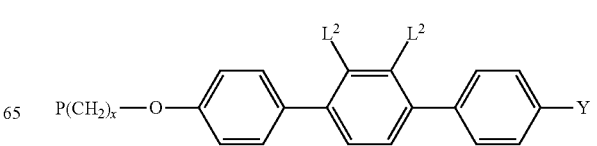

-continued

IId

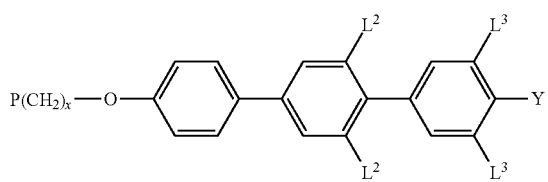

wherein P, x, $L^2$, $L^3$ and Y are as defined in formula I, and in formula Id one of the two groups $L^2$ and one of the two groups $L^3$ can also denote H.

Especially preferred are compounds of formula I1a-d wherein Y is CN, furthermore those wherein $L^2$ and $L^3$ denote F or $CH_3$, most preferably F.

The synthesis of the compounds of formula I and its subformulae can be carried out analogously to the illustrative reactions shown below or in the examples. The preparation of further compounds according to the invention can also be carried out by other methods known per se to the person skilled in the art from the literature. In particular, other catalysts can be used.

For example, the compounds of formula I can be synthesized according to or in analogy to the methods as illustrated in Schemes 1 and 2, wherein o is an integer from 1-12, preferably 3, 4, 5 6.

Scheme 1

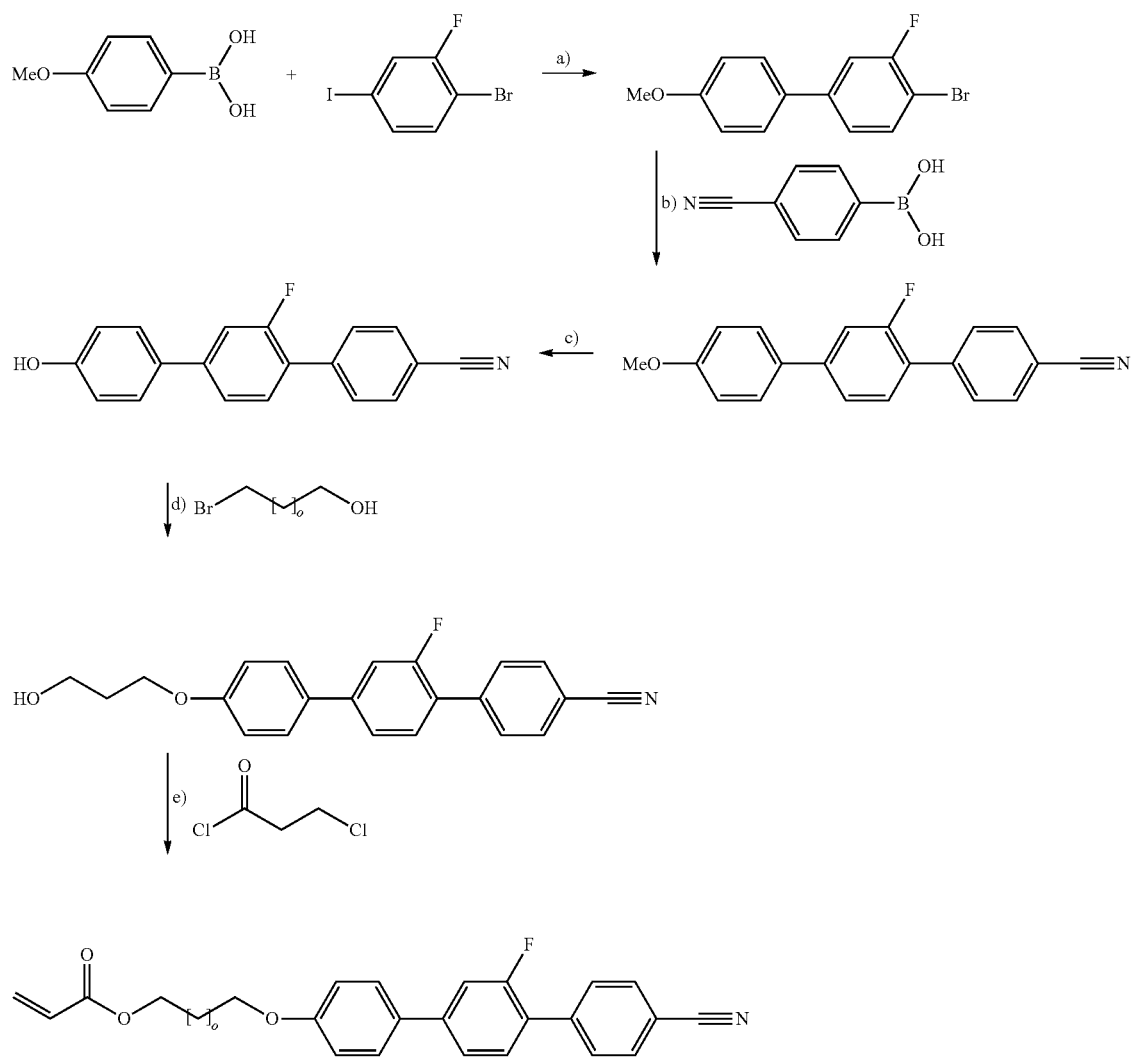

Conditions:
a) Pd(dppf)$_2$Cl$_2$ (II), KH$_2$PO$_4$, 1,4-dioxane 40° C., 2.5 h
b) Pd(dppf)$_2$Cl$_2$ (II), KH$_2$PO$_4$, 1,4-dioxane 100° C., 3 h
c) BBr$_3$, DMC, -30° C. to -20° C., 4 h
d) K$_2$CO$_3$, NaI, Butanone, 80° C., 24 h
e) DCM, NEt$_3$, DMAP, 15° C., Chloropropionyl Chloride, 15-20° C.

Scheme 2

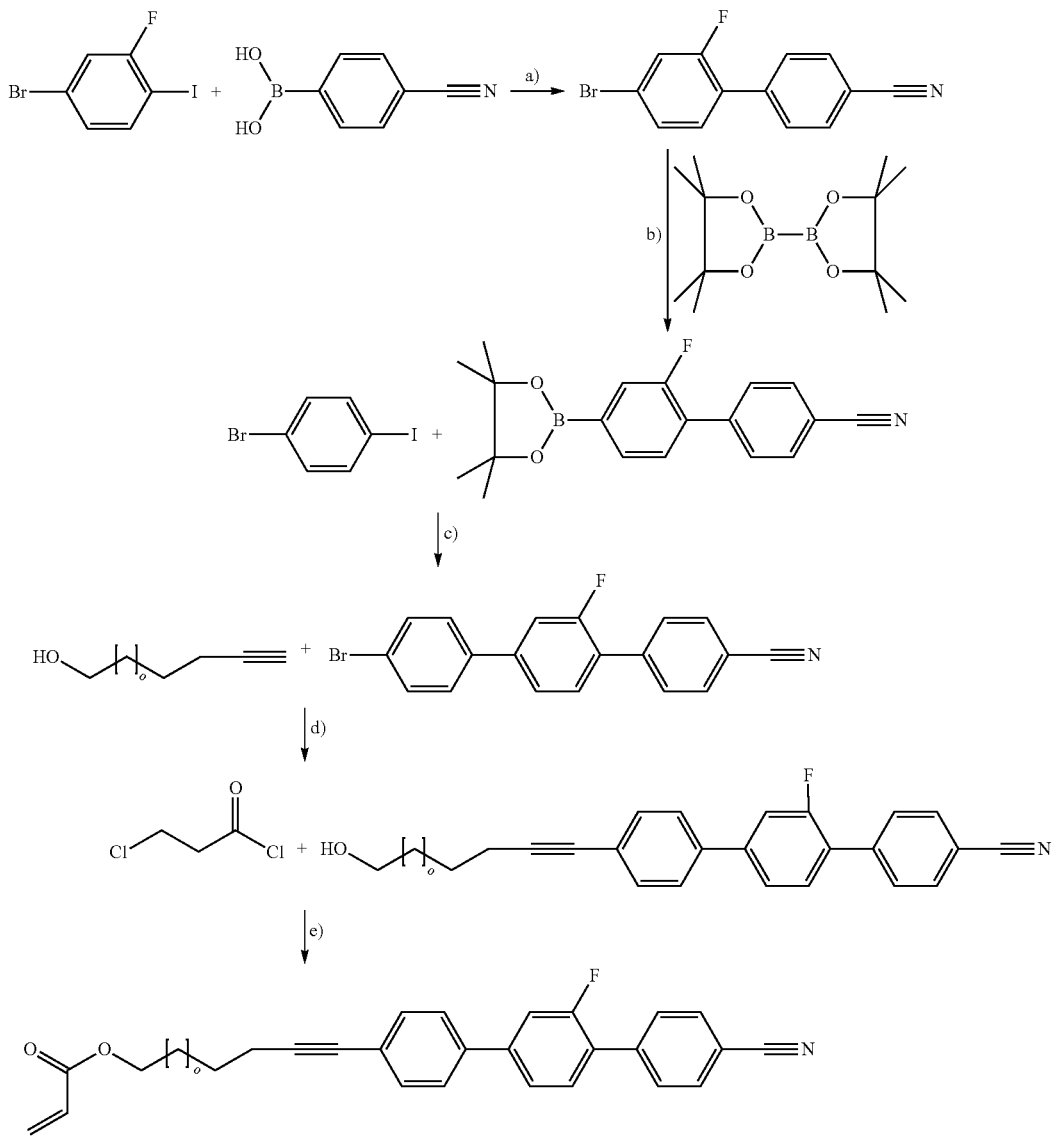

Conditions:
a) Pd(dppf)₂Cl₂ (II), K₂CO₃, 1,2-Dimethoxyethane:Water (2:1), 60° C., 24 h
b) Bis(pinacolato)diboron, Pd(OAc)₂, DPPF, THF, 60° C., 24 h
c) Pd(dppf)₂Cl₂ (II), K(OAc)₂, 1,4-Dioxane:Water (2:1), 40° C., 2 h
d) Pd(PPh₃)₂Cl₂ (II), Diisopropylamine, THF, 90° C., 4.5 h
e) DCM, NEt₃, DMAP, 15° C., Chloropropionyl Chloride, 15-20° C.

Another object of the invention is an RM mixture comprising two or more RMs, at least one of which is a compound of formula I.

Preferably the RM mixture comprises one or more RMs having only one polymerisable functional group (monoreactive RMs), at least one of which is a compound of formula I, and one or more RMs having two or more polymerisable functional groups (di- or multireactive RMs).

The di- or multireactive RMs are preferably selected of formula II

P¹-Sp¹-MG-Sp²-P²    II wherein P¹ and P² independently of each other denote a polymerisable group, Sp¹ and Sp² independently of each other are a spacer group or a single bond, and MG is a rod-shaped mesogenic group, which is preferably selected of formula IV

-(A¹-Z¹)ₙ-A²-    IV wherein
A¹ and A² denote, in case of multiple occurrence independently of one another, an aromatic or alicyclic group, which optionally contains one or more heteroatoms selected from N, O and S, and is optionally mono- or polysubstituted by L,
L is P-Sp-, F, Cl, Br, I, —CN, —NO₂, —NCO, —NCS, —OCN, —SCN, —C(=O)NR⁰⁰R⁰⁰⁰, —C(=O)X⁰, —C(=O)OR⁰⁰, —C(=O)R⁰, —NR⁰⁰R⁰⁰⁰, —OH, —SF$_5$, optionally substituted silyl, aryl or heteroaryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H R$^{00}$ and R$^{000}$ independently of each other denote H or alkyl with 1 to 12 C-atoms, X$^0$ is halogen, preferably F or Cl, Z$^1$ denotes, in case of multiple occurrence independently of one another, —O—, —S—, —CO—, —COO—, —OCO—, —S—CO—, —CO—S—, —O—COO—, —CO—NR$^{00}$—, —NR$^{00}$—CO—, —NR$^{00}$—CO—NR$^{000}$, —NR$^{00}$—CO—O—, —O—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_{n1}$—, —CF$_2$CH$_2$—, —CH$_2$CF$_2$—, —CF$_2$CF$_2$—, —CH=N—, —N=CH—, —N=N—, —CH=CR$^{00}$—, —CY$^1$=CY$^2$—, —C≡C—, —CH=CH—COO—, —OCO—CH=CH— or a single bond, preferably —COO—, —OCO— or a single bond, Y$^1$ and Y$^2$ independently of each other denote H, F, Cl or CN, n is 1, 2, 3 or 4, preferably 1 or 2, most preferably 2, n1 is an integer from 1 to 10, preferably 1, 2, 3 or 4.

Preferred groups A$^1$ and A$^2$ include, without limitation, furan, pyrrol, thiophene, oxazole, thiazole, thiadiazole, imidazole, phenylene, cyclohexylene, bicyclooctylene, cyclohexenylene, pyridine, pyrimidine, pyrazine, azulene, indane, fluorene, naphthalene, tetrahydronaphthalene, anthracene, phenanthrene and dithienothiophene, all of which are unsubstituted or substituted by 1, 2, 3 or 4 groups L as defined above.

Particular preferred groups A$^1$ and A$^2$ are selected from 1,4-phenylene, pyridine-2,5-diyl, pyrimidine-2,5-diyl, thiophene-2,5-diyl, naphthalene-2,6-diyl, 1,2,3,4-tetrahydronaphthalene-2,6-diyl, indane-2,5-diyl, bicyclooctylene or 1,4-cyclohexylene wherein one or two non-adjacent CH$_2$ groups are optionally replaced by O and/or S, wherein these groups are unsubstituted or substituted by 1, 2, 3 or 4 groups L as defined above.

Preferred RMs of formula II are selected of formula Ia

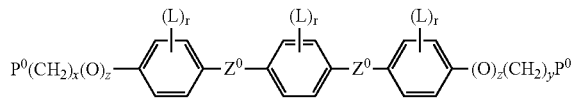

wherein

P$^0$ is, in case of multiple occurrence independently of one another, a polymerisable group, preferably an acryl, methacryl, oxetane, epoxy, vinyl, vinyloxy, propenyl ether or styrene group, Z$^0$ is —COO—, —OCO—, —CH$_2$CH$_2$—, —CF$_2$O—, —OCF$_2$—, —C≡C—, —CH=CH—, —OCO—CH=CH—, —CH=CH—COO—, or a single bond, L has on each occurrence identically or differently one of the meanings given for L$^1$ in formula I, and is preferably, in case of multiple occurrence independently of one another, selected from F, Cl, CN or optionally halogenated alkyl, alkoxy, alkylcarbonyl, alkoxycarbonyl, alkylcarbonyloxy or alkoxycarbonyloxy with 1 to 5 C atoms, r is 0, 1, 2, 3 or 4, x and y are independently of each other 0 or identical or different integers from 1 to 12, z is 0 or 1, with z being 0 if the adjacent x or y is 0.

Very preferred RMs of formula II are selected from the following formulae:

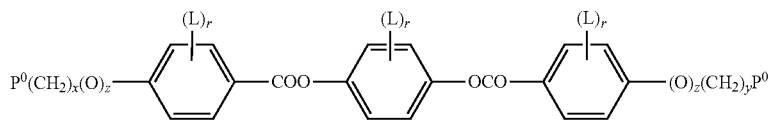

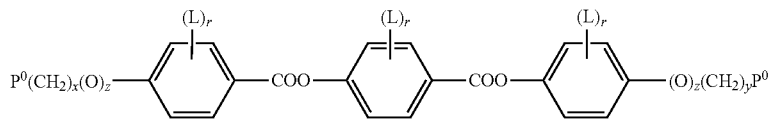

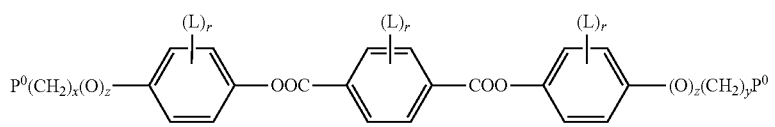

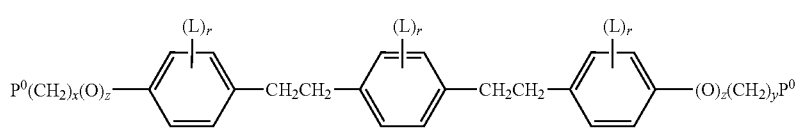

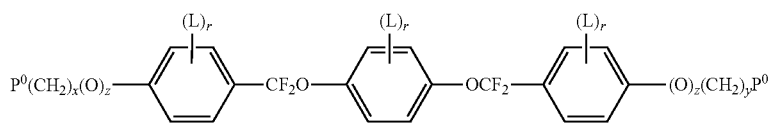

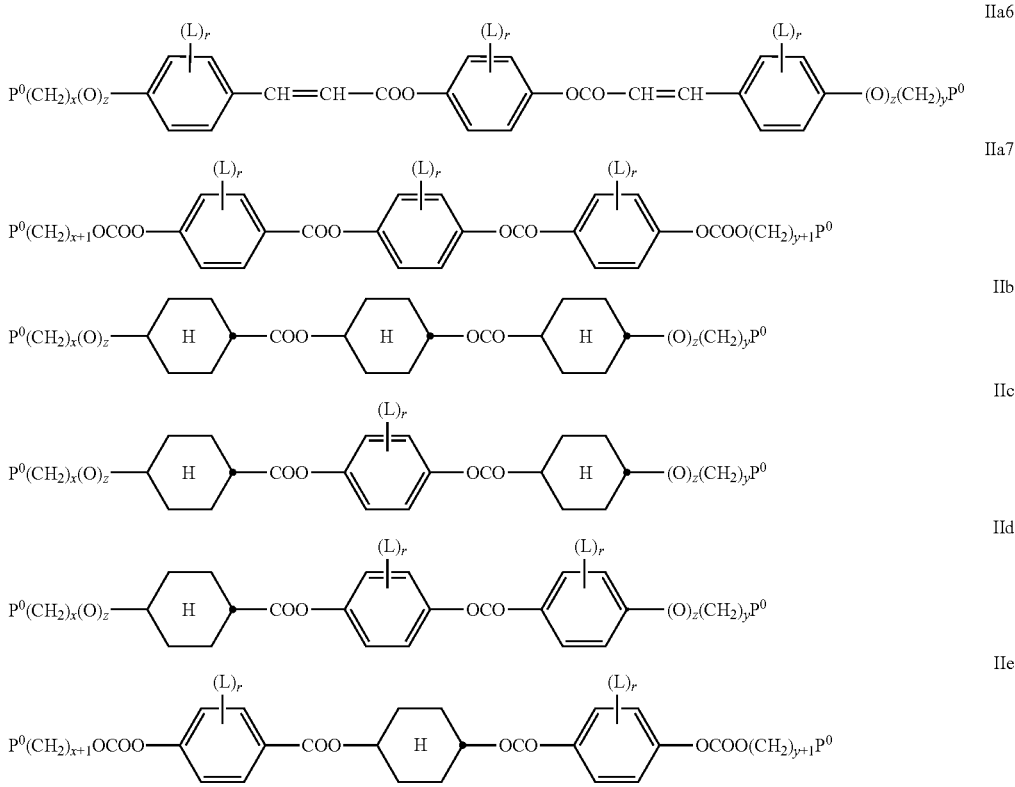

wherein $P^0$, L, r, x, y and z are as defined in formula IIa.

Especially preferred are compounds of formula IIa1, IIa2 and IIa3, in particular those of formula IIa1.

The concentration of di- or multireactive RMs, preferably those of formula II and its subformulae, in the RM mixture is preferably from 30% to 99.9%, very preferably from 50 to 80%.

In another preferred embodiment the RM mixture comprises, in addition to the compounds of formula I, one or more monoreactive RMs. These additional monoreactive RMs are preferably selected from formula III:

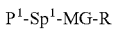
$P^1$-$Sp^1$-MG-R    III wherein $P^1$, $Sp^1$ and MG have the meanings given in formula II, R denotes P-Sp-, F, Cl, Br, I, —CN, —$NO_2$, —NCO, —NCS, —OCN, —SCN, —C(=O)$NR^{00}R^{000}$, —C(=O)X, —C(=O)$OR^0$, —C(=O)$R^{00}$, —$NR^{00}R^{000}$, —OH, —$SF_5$, optionally substituted silyl, straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl, X is halogen, preferably F or Cl, and $R^{00}$ and $R^{000}$ are independently of each other H or alkyl with 1 to 12 C-atoms.

Preferably the RMs of formula III are selected from the following formulae.

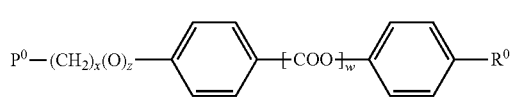
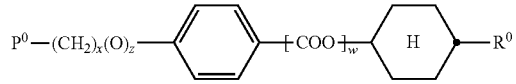
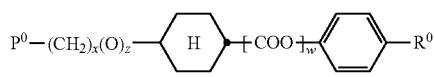
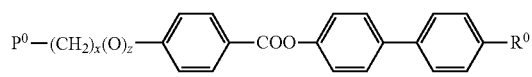
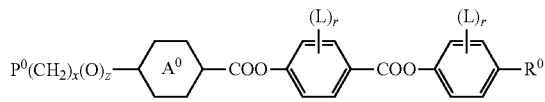
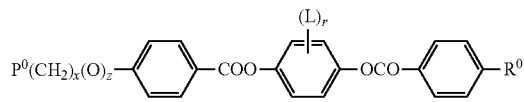

-continued
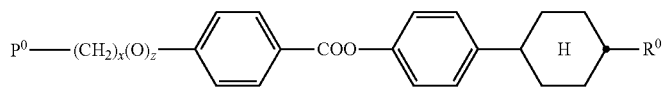
III7
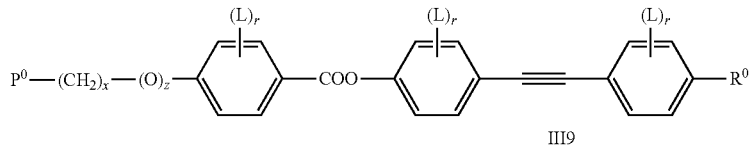
III8
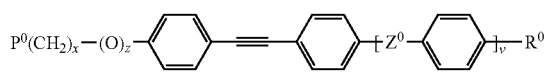
III9
III10
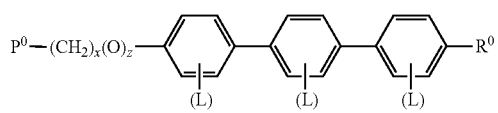
III11
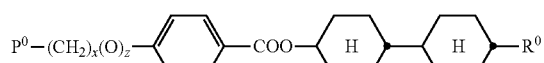
III12
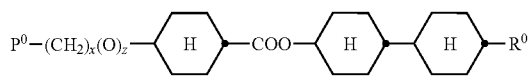
III13
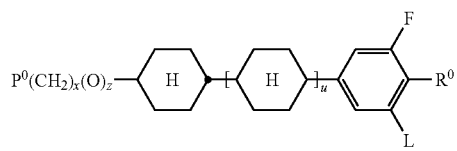
III14
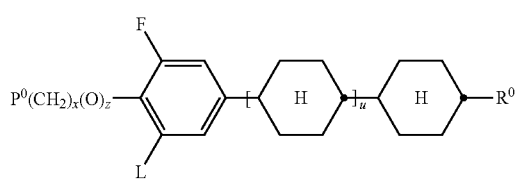
III15
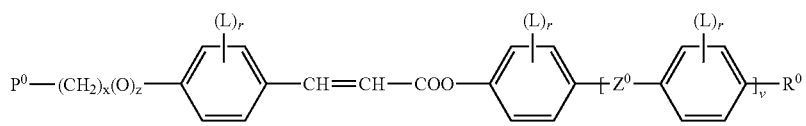
III16
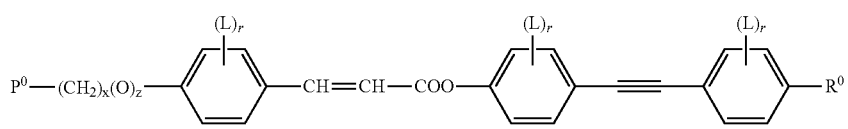
III17
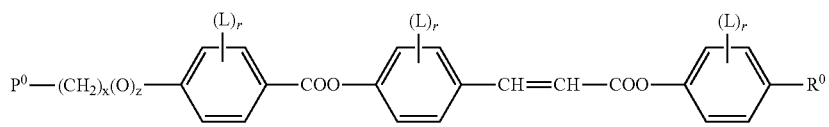
III18
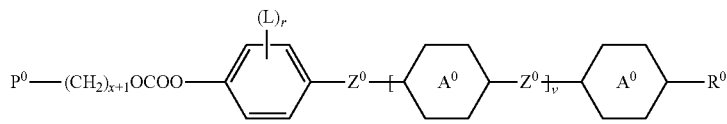
III19
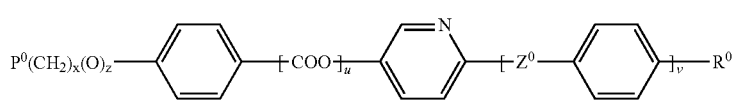
III20
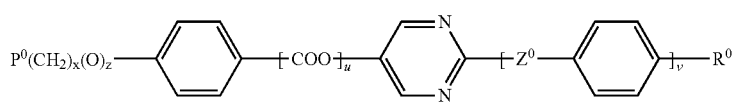
III21

-continued

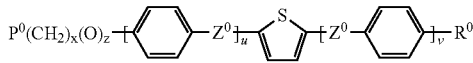
III22

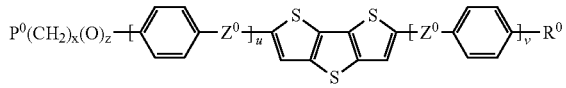
III23

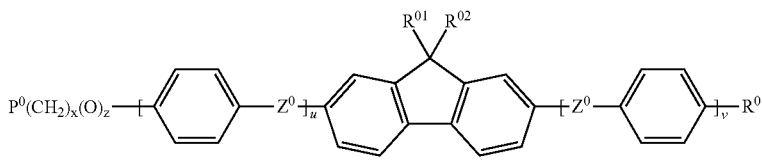
III24

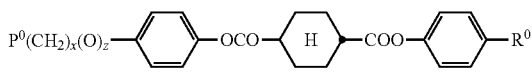
III25

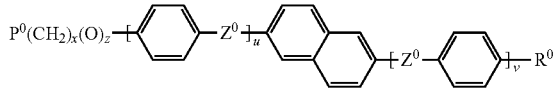
III26

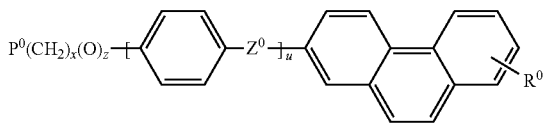
III27 wherein $P^0$, L, r, x, y and z are as defined in formula IIa,
$R^0$ is alkyl, alkoxy, thioalkyl, alkylcarbonyl, alkoxycarbonyl, alkylcarbonyloxy or alkoxycarbonyloxy with 1 or more, preferably 1 to 15 C atoms which is optionally fluorinated, or denotes $Y^0$ or $P-(CH_2)_y-(O)_z-$,
$X^0$ is $-O-$, $-S-$, $-CO-$, $-COO-$, $-COO-$, $-O-COO-$, $-CO-NR^{01}-$, $-NR^{01}-CO-$, $-NR^{01}-CO-NR^{01}-$, $-OCH_2-$, $-CH_2O-$, $-SCH_2-$, $-CH_2S-$, $-CF_2O-$, $-OCF_2-$, $-CF_2S-$, $-SCF_2-$, $-CF_2CH_2-$, $-CH_2CF_2-$, $-CF_2CF_2-$, $-CH=N-$, $-N=CH-$, $-N=N-$, $-CH=CR^{01}-$, $-CF=CF-$, $-C\equiv C-$, $-CH=CH-COO-$, $-OCO-CH=CH-$ or a single bond
$Y^0$ is F, Cl, CN, $NO_2$, $OCH_3$, OCN, SCN, $SF_5$, optionally fluorinated alkylcarbonyl, alkoxycarbonyl, alkylcarbonyloxy or alkoxycarbonyloxy with 1 to 4 C atoms, or mono- oligo- or polyfluorinated alkyl or alkoxy with 1 to 4 C atoms,
$A^0$ is, in case of multiple occurrence independently of one another, 1,4-phenylene that is unsubstituted or substituted with 1, 2, 3 or 4 groups L, or trans-1,4-cyclohexylene,
$R^{01,02}$ are independently of each other H, $R^0$ or $Y^0$,
u and v are independently of each other 0, 1 or 2,
w is 0 or 1,
and wherein the benzene and napthalene rings can additionally be substituted with one or more identical or different groups L.

Especially preferred are compounds of formula III1, III2, III3, III4, III5, III6, III7, III8, III9 and III10, in particular those of formula III1, III4, III6, III7 and III8.

The concentration of all monoreactive RMs, including those of formula I, in the RM mixture is preferably from 1 to 90%, very preferably from 10 to 70%.

The RM mixture preferably exhibits a nematic LC phase, or a smectic LC phase and a nematic LC phase, very preferably a nematic LC phase at room temperature.

In formulae I, II, III and their preferred subformulae, L and $L^{1-3}$ are preferably selected from F, Cl, CN, $NO_2$ or straight chain or branched alkyl, alkoxy, alkylcarbonyl, alkoxycarbonyl, alkylcarbonlyoxy or alkoxycarbonyloxy with 1 to 12 C atoms, wherein the alkyl groups are optionally perfluorinated, or P-Sp-.

Very preferably L and $L^{1-3}$ are selected from F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, in particular F, Cl, ON, $CH_3$, $C_2H_5$, $C(CH_3)_3$, $CH(CH_3)_2$, $OCH_3$, $COCH_3$ or $OCF_3$, most preferably F, Cl, $CH_3$, $C(CH_3)_3$, $OCH_3$ or $COCH_3$, or P-Sp-.

A substituted benzene ring of the formula

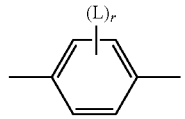

is preferably

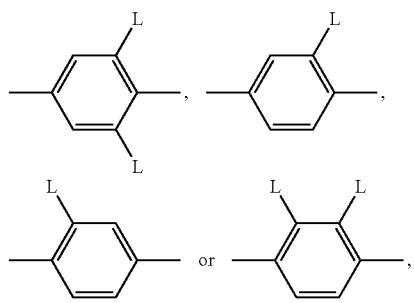

with L having each independently one of the meanings given above.

In formulae I, II, III and their preferred subformulae, an alkyl or alkoxy radical, i.e. where the terminal $CH_2$ group is replaced by $-O-$, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkyl group wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

In an alkyl group wherein one CH$_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more CH$_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

An alkyl or alkenyl group that is monosubstituted by CN or CF$_3$ is preferably straight-chain. The substitution by CN or CF$_3$ can be in any desired position.

An alkyl or alkenyl group that is at least monosubstituted by halogen is preferably straight-chain. Halogen is preferably F or Cl, in case of multiple substitution preferably F. The resulting groups include also perfluorinated groups. In case of monosubstitution the F or Cl substituent can be in any desired position, but is preferably in co-position. Examples for especially preferred straight-chain groups with a terminal F substituent are fluoromethyl, 2-fluoroethyl, 3-fluoropropyl, 4-fluorobutyl, 5-fluoropentyl, 6-fluorohexyl and 7-fluoroheptyl. Other positions of F are, however, not excluded.

$R^{oo}$ and $R^{ooo}$ are preferably selected from H, straight-chain or branched alkyl with 1 to 12 C atoms.

—CY$^1$=CY$^2$— is preferably —CH=CH—, —CF=CF— or —CH=C(CN)—.

Halogen is F, Cl, Br or I, preferably F or Cl.

R, R$^0$, R$^1$ and R$^2$ can be an achiral or a chiral group. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), isopropoxy, 2-methyl-propoxy and 3-methylbutoxy.

In formulae I, II, III and their preferred subformulae, the polymerisable groups P, P$^1$, P$^2$ and P$^0$ denote a group that is capable of participating in a polymerisation reaction, like radical or ionic chain polymerisation, polyaddition or polycondensation, or capable of being grafted, for example by condensation or addition, to a polymer backbone in a polymer analogous reaction. Especially preferred are polymerisable groups for chain polymerisation reactions, like radical, cationic or anionic polymerisation. Very preferred are polymerisable groups comprising a C—C double or triple bond, and polymerisable groups capable of polymerisation by a ring-opening reaction, like oxetanes or epoxides.

Suitable and preferred polymerisable groups P, P$^1$, P$^2$ and P$^0$ include, without limitation, CH$_2$=CW$^1$—COO—, CH$_2$=CW$^1$—CO—,

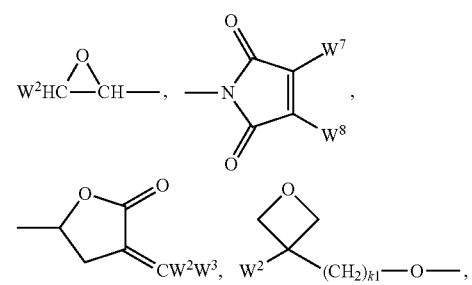

CH$_2$=CW$^2$—(O)$_{k1}$—, CH$_3$—CH=CH—O—, (CH$_2$=CH)$_2$CH—OCO—, (CH$_2$=CH—CH$_2$)$_2$CH—

OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, Cl or CH$_3$, W$^2$ and W$^3$ being independently of each other H or alkyl with 1 to 5 C-atoms, in particular H, methyl, ethyl or n-propyl, W$^4$, W$^5$ and W$^6$ being independently of each other Cl, oxaalkyl or oxacarbonylalkyl with 1 to 5 C-atoms, W$^7$ and W$^8$ being independently of each other H, Cl or alkyl with 1 to 5 C-atoms, Phe being 1,4-phenylene that is optionally substituted, preferably by one or more groups L as defined above (except for the meaning P-Sp-), and k$_1$ and k$_2$ being independently of each other 0 or 1.

Very preferred polymerisable groups P, P$^1$, P$^2$ and P$^0$ are selected from CH$_2$=CW$^1$—COO—, CH$_2$=CW$^1$—CO—,

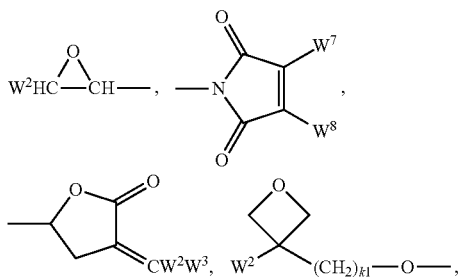

(CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, F, Cl or CH$_3$, W$^2$ and W$^3$ being independently of each other H or alkyl with 1 to 5 C-atoms, in particular H, methyl, ethyl or n-propyl, W$^4$, W$^5$ and W$^6$ being independently of each other Cl, oxaalkyl or oxacarbonylalkyl with 1 to 5 C-atoms, W$^7$ and W$^8$ being independently of each other H, Cl or alkyl with 1 to 5 C-atoms, Phe being 1,4-phenylene that is optionally substituted preferably by one or more groups L as defined above (except for the meaning P-Sp-), and k$_1$ and k$_2$ being independently of each other 0 or 1.

Most preferred polymerisable groups P, P$^1$, P$^2$ and P$^0$ are selected from CH$_2$=CH—COO—, CH$_2$=C(CH$_3$)—COO—, CH$_2$=CF—COO—, (CH$_2$=CH)$_2$CH—OCO—, (CH$_2$=CH)$_2$CH—O—,

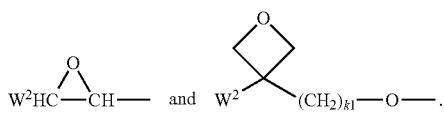

Further preferably P, P$^1$, P$^2$ and P$^0$ are selected from the group consisting of vinyloxy, acrylate, methacrylate, fluoroacrylate, chloroacrylate, oxetane and epoxide groups, and particularly preferably denote an acrylate, methacrylate or oxetane group.

Polymerisation can be carried out according to methods that are known to the ordinary expert and described in the literature, for example in D. J. Broer; G. Challa; G. N. Mol, *Macromol. Chem*, 1991, 192, 59.

In formulae I, II, III and their preferred subformulae, the spacer groups Sp, Sp$^1$ and Sp$^2$ are preferably selected of formula Sp'-X', such that e.g. P-Sp- is P-Sp'-X'—, wherein Sp' is alkylene with 1 to 20 C atoms, preferably 1 to 12 C-atoms, which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —NR$^0$—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, R$^0$ and R$^{00}$ are independently of each other H or alkyl with 1 to 12 C-atoms, and Y$^1$ and Y$^2$ are independently of each other H, F, Cl or CN.

X' is preferably —O—, —S—CO—, —COO—, —OCO—, —O—COO—, —CO—NR$^0$—, —NR$^0$—CO—, —NR$^0$—CO—NR$^0$— or a single bond.

Typical groups Sp' are, for example, —(CH$_2$)$_{p1}$—, —(CH$_2$CH$_2$O)$_{q1}$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_{p1}$—, with p1 being an integer from 2 to 12, q1 being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxy-butylene, ethylene-thioethylene, ethylene-N-methyl-iminoethylene, 1-methylalkylene, ethenylene, propenylene and butenylene for example.

Further preferred are compounds wherein the polymerisable group is directly attached to the mesogenic group without a spacer group Sp.

In case of compounds with multiple groups P-Sp-, P$^1$—Sp$^1$- etc., the multiple polymerisable groups P, P$^1$ and the multiple spacer groups Sp, Sp$^1$ can be identical or different from one another.

In another preferred embodiment the reactive compounds comprise one or more terminal groups R$^{0,1,2}$ or substituents L or L$^{1-3}$ that are substituted by two or more polymerisable groups P or P-Sp- (multifunctional polymerisable groups). Suitable multifunctional polymerisable groups of this type are disclosed for example in U.S. Pat. No. 7,060,200 B1 oder US 2006/0172090 A1. Very preferred are compounds comprising one or more multifunctional polymerisable groups selected from the following formulae:

| —X-alkyl-CHP$^1$—CH$_2$—CH$_2$P$^2$ | P1 |
| —X'-alkyl-C(CH$_2$P$^1$)(CH$_2$P$^2$)—CH$_2$P$^3$ | P2 |
| —X'-alkyl-CHP$^1$CHP$^2$—CH$_2$P$^3$ | P3 |
| —X'-alkyl-C(CH$_2$P$^1$)(CH$_2$P$^2$)—C$_{aa}$H$_{2aa+1}$ | P4 |

—X'-alkyl-CHP$^1$—CH$_2$P$^2$ P5

—X'-alkyl-CHP$^1$P$^2$ P5

—X'-alkyl-CP$^1$P$^2$—C$_{aa}$H$_{2aa+1}$ P6

—X'-alkyl-C(CH$_2$P$^1$)(CH$_2$P$^2$)—CH$_2$OCH$_2$—C(CH$_2$P$^3$)(CH$_2$P$^4$)CH$_2$P$^5$ P7

—X'-alkyl-CH((CH$_2$)$_{aa}$P$^1$)((CH$_2$)$_{bb}$P$^2$) P8

—X'-alkyl-CHP$^1$CHP$^2$—C$_{aa}$H$_{2aa+1}$ P9 wherein
alkyl is straight-chain or branched alkylene having 1 to 12 C-atoms which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^o$—, —SiR$^o$R$^{oo}$—, —CO—, —COO—, —OCO—, —O—CO—O—, —S—CO—, —CO—S—, —SO$_2$—, —CO—NR$^o$—, —NR$^o$—CO—, —NR$^o$—CO—NR$^{oo}$—, —CY$^1$=CY$^2$— or —C≡C— in such a manner that O and/or S atoms are not linked directly to one another, with R$^o$ and R$^{oo}$ having the meanings given above, or denotes a single bond,
aa and bb are independently of each other 0, 1, 2, 3, 4, 5 or 6,
X' is as defined above, and
P$^{1-5}$ independently of each other have one of the meanings given for P above.

Another object of the invention is an RM formulation comprising one or more compounds of formula I, or comprising an RM mixture, as described above and below, and further comprising one or more solvents and/or additives.

In a preferred embodiment the RM formulation comprises one or more additives selected from the group consisting of polymerisation initiators, surfactants, stabilisers, catalysts, sensitizers, inhibitors, chain-transfer agents, co-reacting monomers, surface-active compounds, lubricating agents, wetting agents, dispersing agents, hydrophobing agents, adhesive agents, flow improvers, degassing or defoaming agents, deaerators, diluents, reactive diluents, auxiliaries, colourants, dyes, pigments and nanoparticles.

In another preferred embodiment the RM formulation comprises one or more additives selected from monoreactive polymerisable non-mesogenic compounds. The amount of these additives in the RM formulation is preferably from 0 to 30%, very preferably from 0 to 15%. Typical examples of such additives are alkylacrylates and alkylmethacrylates.

In another preferred embodiment the RM formulation comprises one or more additives selected from di- or multireactive polymerisable non-mesogenic compounds, alternatively or in addition to the di- or multireactive polymerisable mesogenic compounds. The amount of these additives in the RM formulation is preferably from 0 to 30%, very preferably from 0 to 15%. Typical examples of direactive non-mesogenic compounds are alkyldiacrylates or alkyldimethacrylates with alkyl groups of 1 to 20 C atoms. Typical examples of multireactive non-mesogenic compounds are trimethylpropanetrimethacrylate or pentaerythritoltetraacrylate.

In another preferred embodiment the RM formulation comprises one or more additives selected from polymeric binders or precursors thereof, and/or one or more dispersion auxiliaries. Suitable binders and dispersion auxiliaries are disclosed for example in WO 96/02597. Preferably, however, the RM formulation does not contain a binder or dispersion auxiliary.

In another preferred embodiment the RM formulation comprises one or more solvents, which are preferably selected from organic solvents. The solvents are preferably selected from ketones such as acetone, methyl ethyl ketone, methyl propyl ketone, methyl isobutyl ketone or cyclohexanone; acetates such as methyl, ethyl or butyl acetate or methyl acetoacetate; alcohols such as methanol, ethanol or isopropyl alcohol; aromatic solvents such as toluene or xylene; alicyclic hydrocarbons such as cyclopentane or cyclohexane; halogenated hydrocarbons such as di- or trichloromethane; glycols or their esters such as PGMEA (propyl glycol monomethyl ether acetate), γ-butyrolactone.

It is also possible to use binary, ternary or higher mixtures of the above solvents.

In case the RM formulation contains one or more solvents, the total concentration of all solids, including the RMs, in the solvent(s) is preferably from 10 to 60%.

Polymerisation of the RMs is preferably carried out in the presence of an initiator absorbing at the wavelength of the actinic radiation. For this purpose, preferably the RM formulation contains one or more polymerisation initiators.

For example, when polymerising by means of UV light, a photoinitiator can be used that decomposes under UV irradiation to produce free radicals or ions that start the polymerisation reaction. For polymerising acrylate or methacrylate groups preferably a radical photoinitiator is used. For polymerising vinyl, epoxide or oxetane groups preferably a cationic photoinitiator is used. It is also possible to use a thermal polymerisation initiator that decomposes when heated to produce free radicals or ions that start the polymerisation. Typical radical photoinitiators are for example the commercially available Irgacure® or Darocure® (Ciba AG). for example Irgacure 651, Irgacure 907 or Irgacure 369. A typical cationic photoinitiator is for example UVI 6974 (Union Carbide).

The concentration of the polymerisation initiator in the RM formulation is preferably from 0.01 to 5%, very preferably from 0.1 to 3.

In another preferred embodiment of the present invention the RM formulation contains one or more surfactants. The surfactants are selected such that they to promote planar surface alignment of the LC molecules when preparing the polymer film. Suitable surfactants are described for example in J. Cognard, Mol. Cryst. Liq. Cryst. 78, Supplement 1, 1-77 (1981).

Especially preferred are non-ionic surfactants, preferably polymerisable or unpolymerisable fluorocarbon surfactants, like for example Fluorad® FC-171 (from 3M Co.) or Zonyl FSN® (from DuPont), or Fluorad® FX-13 or FX-14 (from 3M Co.).

The concentration of the surfactants in the RM formulation is preferably from 0.1 to 5%, very preferably from 0.1 to 1%.

Preferably the RM formulation comprises:
 1 to 50% of compounds of formula I,
 1 to 60% of di- or multireactive RMs,
 0 to 80% monoreactive RMs,
 0 to 5% of one or more polymerisation initiators,
 0 to 5% of one or more surfactants.

The preparation of polymers according to this invention can be carried out by methods that are known to the skilled person and described in the literature, for example in D. J. Broer; G. Challa; G. N. Mol, *Macromol. Chem,* 1991, 192, 59.

Typically the RM, RM mixture or RM formulation is coated or otherwise applied onto a substrate, for example by a coating or printing method, where the RMs are aligned into uniform orientation. Preferably the RMs are aligned into planar alignment, i.e. with the long molecular axes of the RM molecules aligned parallel to the substrate.

The aligned RMs are then polymerised in situ, preferably at a temperature where they exhibit an LC phase, for example by exposure to heat or actinic radiation. Preferably the RMs are polymerised by photo-polymerisation, very preferably by UV-photopolymerisation, to fix the uniform alignment. If necessary, uniform alignment can be promoted by additional means like shearing or annealing of the RMs, surface treatment of the substrate, or adding surfactants to the RM mixture or the RM formulation.

As substrate for example glass or quartz sheets or plastic films can be used. It is also possible to put a second substrate on top of the coated material prior to and/or during and/or after polymerisation. The substrates can be removed after polymerisation or not. When using two substrates in case of curing by actinic radiation, at least one substrate has to be transmissive for the actinic radiation used for the polymerisation. Isotropic or birefringent substrates can be used. In case the substrate is not removed from the polymerised film after polymerisation, preferably isotropic substrates are used.

Suitable and preferred plastic substrates are for example films of polyester such as polyethyleneterephthalate (PET) or polyethylene-naphthalate (PEN), polyvinylalcohol (PVA), polycarbonate (PC) or triacetylcellulose (TAC), very preferably PET or TAC films. As birefringent substrates for example uniaxially stretched plastics film can be used. PET films are commercially available for example from DuPont Teijin Films under the trade name Melinex®.

Preferably the RMs and the other solid additives are dissolved in a solvent. The solution is then coated or printed onto the substrate, for example by spin-coating or printing or other known techniques, and the solvent is evaporated off before polymerisation. In many cases it is suitable to heat the coated solution in order to facilitate the evaporation of the solvent.

The RM formulation can be applied onto the substrate by conventional coating techniques like spin-coating or blade coating. It can also be applied to the substrate by conventional printing techniques which are known to the expert, like for example screen printing, offset printing, reel-to-reel printing, letter press printing, gravure printing, rotogravure printing, flexographic printing, intaglio printing, pad printing, heat-seal printing, ink-jet printing or printing by means of a stamp or printing plate.

The RM formulation preferably exhibits planar alignment. This can be achieved for example by rubbing treatment of the substrate, by shearing the material during or after coating, by annealing the material before polymerisation, by application of an alignment layer, by applying a magnetic or electric field to the coated material, or by the addition of surface-active compounds to the formulation. Reviews of alignment techniques are given for example by I. Sage in "Thermotropic Liquid Crystals", edited by G. W. Gray, John Wiley & Sons, 1987, pages 75-77; and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

It is also possible to apply an alignment layer onto the substrate and provide the RM mixture or RM formulation onto this alignment layer. Suitable alignment layers are known in the art, like for example rubbed polyimide or alignment layers prepared by photoalignment as described in U.S. Pat. No. 5,602,661, U.S. Pat. No. 5,389,698 or U.S. Pat. No. 6,717,644.

It is also possible to induce or improve alignment by annealing the RMs at elevated temperature, but below their clearing temperature, prior to polymerisation.

Polymerisation is achieved for example by exposing the polymerisable material to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation. As a source for actinic radiation for example a single UV lamp or a set of UV lamps can be used. When using a high lamp power the curing time can be reduced. Another possible source for actinic radiation is a laser, like for example a UV, IR or visible laser.

The curing time depends, inter alia, on the reactivity of the RMs, the thickness of the coated layer, the type of polymerisation initiator and the power of the UV lamp. The curing time is preferably ≤5 minutes, very preferably ≤3 minutes, most preferably ≤1 minute. For mass production short curing times of ≤30 seconds are preferred.

The polymerisation process is not limited to one curing step. It is also possible to carry out polymerisation by two or more steps, in which the film is exposed to two or more lamps of the same type, or two or more different lamps in sequence. The curing temperature of different curing steps might be the same or different. The lamp power and dose from different lamps might also be the same or different. In addition to the conditions described above, the process steps may also include a heat step between exposure to different lamps, as described for example in JP 2005-345982 A and JP 2005-265896 A.

Preferably polymerisation is carried out in air, but polymerising in an inert gas atmosphere like nitrogen or argon is also possible.

The thickness of a polymer film according to the present invention is preferably from 0.2 to 10 microns, very preferably from 0.3 to 5 microns, most preferably from 0.5 to 3 microns.

The RMs, RM mixtures and polymers of the present invention can be used in optical, electrooptical or electronic devices ort components thereof. For example, they can be used in optical retardation films, polarizers, compensators, beam splitters, reflective films, alignment layers, colour filters, antistatic protection sheets, or electromagnetic interference protection sheets, polarization controlled lenses for autostereoscopic 3D displays, and IR reflection films for window applications.

The RMs, RM mixtures, polymers and device components of the present invention can be used for example in devices selected from electrooptical displays, especially liquid crystal displays (LCDs), autostereoscopic 3D displays, organic light emitting diodes (OLEDs), optical data storage devices, and window applications.

The RMs, RM mixtures, polymers and device components of the present invention can be used outside the switchable LC cell of an LCD or between the substrates, usually glass substrates, forming the switchable LC cell and containing the switchable LC medium (incell application).

The RMs, RM mixtures, polymers and device components of the present invention can be used in conventional LC displays, for example displays with vertical alignment like the DAP (deformation of aligned phases), ECB (electrically controlled birefringence), CSH (colour super homeotropic), VA (vertically aligned), VAN or VAC (vertically aligned nematic or cholesteric), MVA (multi-domain vertically aligned), PVA (patterned vertically aligned) or PSVA (polymer stabilised vertically aligned) mode; displays with bend or hybrid alignment like the OCB (optically compensated bend cell or optically compensated birefringence), R—OCB (reflective OCB), HAN (hybrid aligned nematic) or pi-cell (π-cell) mode; displays with twisted alignment like the TN (twisted nematic), HTN (highly twisted nematic), STN (super twisted nematic), AMD-TN (active matrix driven TN) mode; displays of the IPS (in plane switching) mode, or displays with switching in an optically isotropic phase.

The RMs, RM mixtures and polymers of the present invention can be used for various types of optical films, like twisted optical retarders, reflective polarisers and brightness enhancement films.

The thickness of a polymer film with reduced sheet resistance, including the above mentioned preferred embodiments, is preferably from 0.2 to 5, very preferably from 0.5 to 3 microns.

Above and below, percentages are percent by weight unless stated otherwise. All temperatures are given in degrees Celsius. m.p. denotes melting point, cl.p. denotes clearing point, $T_g$ denotes glass transition temperature. Furthermore, C=crystalline state, N=nematic phase, S=smectic phase and I=isotropic phase. The data between these symbols represent the transition temperatures. Δn denotes the optical anisotropy or birefringence (Δn=$n_e$-$n_o$, where $n_o$ denotes the refractive index parallel to the longitudinal molecular axes and $n_e$ denotes the refractive index perpendicular thereto), measured at 589 nm and 20° C. The optical and electrooptical data are measured at 20° C., unless expressly stated otherwise. "Clearing point" and "clearing temperature" mean the temperature of the transition from an LC phase into the isotropic phase.

Unless stated otherwise, the percentages of solid components in an RM mixture or RM formulation as described above and below refer to the total amount of solids in the mixture or formulation, i.e. without any solvents.

Unless stated otherwise, all optical, electrooptical properties and physical parameters like birefringence, permittivity, electrical conductivity, electrical resistivity and sheet resistance, refer to a temperature of 20° C.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The following examples are intended to explain the invention without restricting it. The methods, structures and properties described hereinafter can also be applied or transferred to materials that are claimed in this invention but not explicitly described in the foregoing specification or in the examples.

Example 1

Compound (RM1) was prepared as described below.

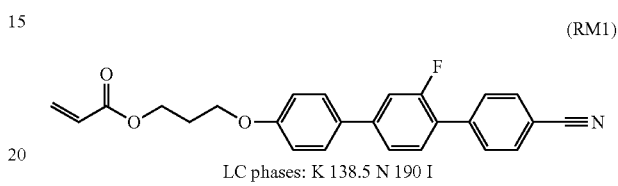

LC phases: K 138.5 N 190 I

Stage 1

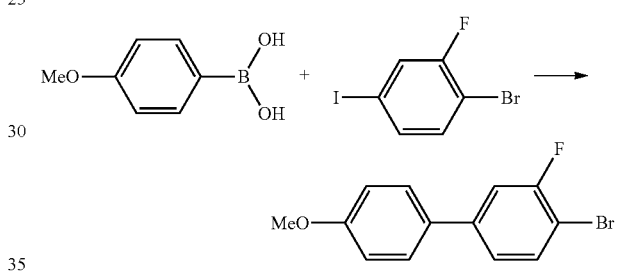

4-Bromo-3-fluoroiodobenzene (200 g, 0.665 mol), 4-methoxybenzeneboronic acid (100.8 g, 0.663 mol), dioxane (1.21), water (600 ml) and potassium phosphate (320 g, 1.51 mol) were ultrasonicated for 30 minutes. [1,1-Bis (diphenylphosphino)ferrocene]dichloropalladium(II) (6.4 g, 8.74 mmol) was added and the mixture heated to 40° C. and held for 2.5 hours. The mixture was cooled, the two layers were separated and the solvent from the organic layer removed in vacuo. The residue was purified by column chromatography eluting with petrol 40-60° C.:DCM 4:1 then petrol 40-60° C.:DCM 3:1. The fractions containing the product were combined and the solvent removed in vacuo. The solid was triturated with petrol 40-60° C. to give the desired product (131.05 g, 70% yield).

Stage 2

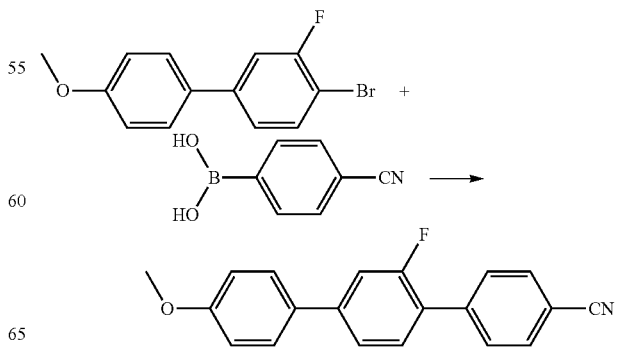

4-Bromo-3-fluoro-4'-methoxy-bipheny (90 g, 0.320 mol), 4-cyanophenylboronic acid (51.75 g, 0.352 mol), dioxane (550 ml), water (275 ml) and potassium phosphate (112 g, 0.528 mol) were ultrasonicated for 30 minutes. [1,1-Bis (diphenylphosphino)ferrocene]dichloropalladium(II) (2.75 g, 3.75 mmol) was added and the mixture heated to 100° C. and held for 3 hours. The mixture was cooled, the two layers were separated and the solvent from the organic layer removed in vacuo. The residue was purified by column chromatography eluting with petrol 40-60° C.:DCM 2:1 then DCM. The fractions containing the product were combined and the solvent removed in vacuo. The solid was crystallised from acetonitrile to give the desired product (65.91 g, 68% yield).
Stage 3

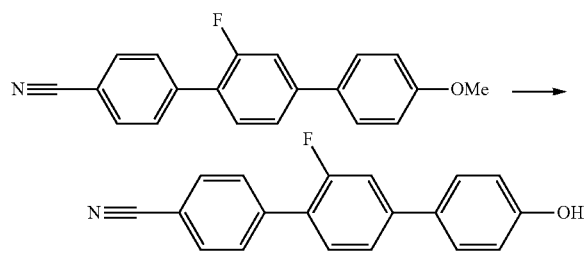

2'-Fluoro-4''-methoxy-[1,1';4',1'']terphenyl-4-carbonitrile (60 g, 0.198 mol) was dissolved in dry DCM (800 ml) and cooled to −25° C. Boron tribromide (116 g, 0.462 mol) was added drop wise over 30 minutes at −30° C. to −20° C. The mixture was stirred for a further 1 hour at −30° C. to −20° C., and then allowed to warm to room temperature. After 4 hours the mixture was cooled to 5° C. Water (500 ml) was slowly added over 1 hour then stirred for a further 1 hour. The solid was filtered off, washed with water (1 L), then azeotroped with toluene (2×100 ml) to give the desired product (57.2 g, 100% yield). The product was used in the next step without further purification.
Stage 4

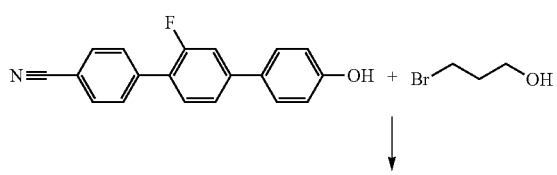

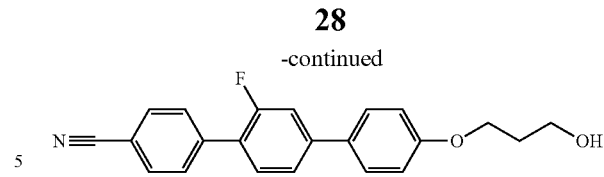

2'-Fluoro-4''-hydroxy-[1,1';4',1'']terphenyl-4-carbonitrile (57.2 g, 0.198 mol), 3-bromopropanol (30.7 g, 0.221 mol), potassium carbonate (41 g, 0.297 mol) sodium iodide (3.7 g, 0.025 mol) and butanone (570 ml) were refluxed for 5 hours. TLC analysis indicated no reaction. Additional potassium carbonate (41 g, 0.297 mol) was added and the mixture heated at 80° C. overnight. TLC analysis indicated ca. 60% conversion to products. Additional potassium carbonate (41 g, 0.297 mol) was added and the mixture refluxed for 6 hours. TLC analysis indicated no change. Additional 3-bromopropanol (15.9, 0.114 mol) was added and the mixture heated at 80° C. overnight. TLC analysis indicated complete conversion to products. The mixture was diluted with acetone (800 ml), filtered hot, and the solvent from the filtrate removed in vacuo. The solid was crystallised from acetonitrile (500 ml), the solid was filtered off, washed with acetonitrile (ca. 200 ml), water (2×200 ml) then acetonitrile (2×200 ml) to give desired product (57.3 g, 83.4% yield).
Stage 5

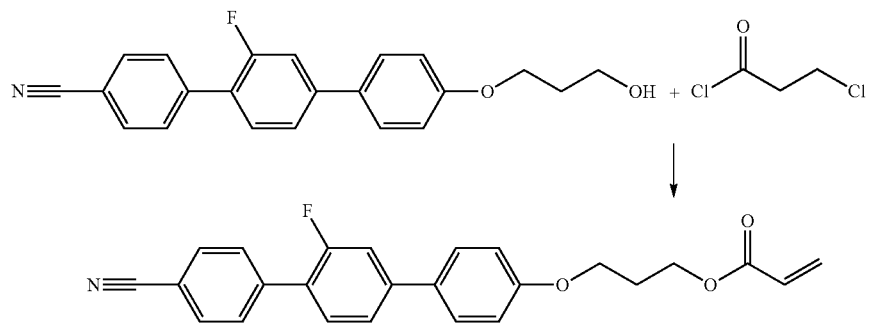

2'-Fluoro-4''-(3-hydroxy-propoxy)-[1,1';4',1'']terphenyl-4-carbonitrile (57.3 g, 0.165 mol), DCM (1.5 L), triethylamine (120 ml, 0.862 mol) and DMAP (few crystals) were stirred at 15° C. 3-chloropropionyl chloride (19 ml, 199 mmol) was added dropwise over 30 minutes at 15° C.-20° C. The mixture was stirred for a further 1 hour at room temperature then heated at 35° C. overnight. Additional 3-chloropropionyl chloride (5 ml, 52 mmol) was added dropwise over 2 hours at room temperature. The mixture was then heated at 35° C. overnight. The mixture was cooled. Water (300 ml) and concentrated hydrochloric acid (110 ml) were mixed and added to the reaction mixture. The two layers were separated and the aqueous layer extracted with DCM (2×50 ml). The organic extracts were dried over anhydrous sodium sulphate, filtered and the solvent from the filtrate removed in vacuo. The residue was purified by vacuum flash chromatography on silica (500 g) eluting with DCM to give a yellow solid. The solid was again purified by vacuum flash chromatography on silica (500 g) eluting with DCM to give a colourless solid. The solid was recrystallized from acetonitrile (600 ml) to give desired product (52 g, 79% yield).

Example 2

Compound (RM2) was prepared as described below.

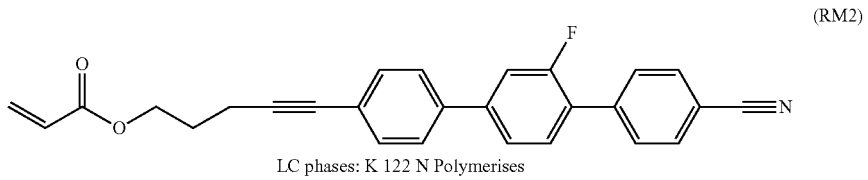 [SMILES: C=CC(=O)OCCCC#Cc1ccc(-c2ccc(-c3ccc(C#N)cc3)c(F)c2)cc1]

(RM2)

LC phases: K 122 N Polymerises

Stage 1

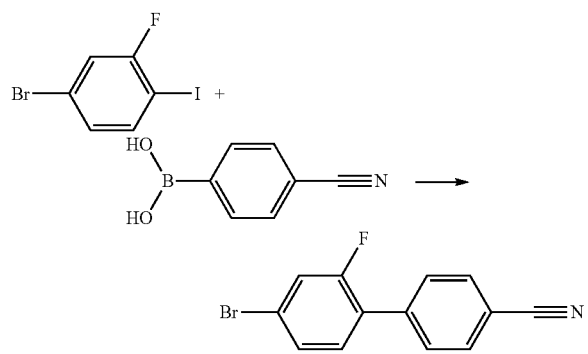

4-Bromo-2-fluoroiodobenzene (72.2 g, 240 mmol), 4-cyanobenzeneboronic acid (35.2 g, 240 mmol), dimethoxyethane (300 ml), water (150 ml) and potassium carbonate (50 g, 362 mmol) were ultrasonicated for 15 minutes. [1,1-Bis(diphenylphosphino)ferrocene]dichloropalladium (II) (1.2 g, 1.7 mmol) was added and the mixture heated to 80° C. for 2.5 hours and a further 17 hours at 60° C. The mixture was cooled, water (360 ml) was added and the mixture acidified cautiously with concentrated HCl (60 ml). The two layers were separated and the aqueous layer extracted with MTBE (1000 ml and 2×200 ml). The combined organic extracts were dried over anhydrous sodium sulphate, filtered and the solvent from the filtrate removed in vacuo. The residue was purified by vacuum flash chromatography eluting with toluene/heptane 1:1. The fractions containing the product were combined and the solvent removed in vacuo to give the desired product (35.4 g, 53% yield).

Stage 2

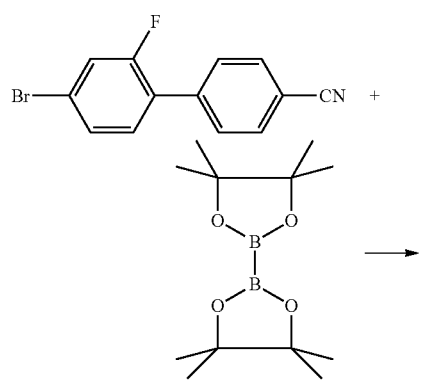

-continued

4'-Bromo-2'-fluoro-biphenyl-4-carbonitrile (27.6 g, 100 mmol), bis(pinacolato)diborane (25.4 g, 100 mmol), potassium acetate (34 g, 360 mmol), palladium acetate (450 mg, 2 mmol), 1,1-Bis(diphenylphosphino)ferrocene (1.11 g, 2 mmol) and THF (250 ml) were ultrasonicated for 30 minutes. The mixture was refluxed for 5 hours then stirred at 60° C. overnight. The mixture was cooled. Water (500 ml) was added. The mixture was extracted with DCM (300 and 2×200 ml). The solvent from the organic layer was removed in vacuo. The residue was dissolved in DCM (200 ml) and purified by vacuum flash chromatography on silica (220 g) eluting with DCM. The solvent was removed in vacuo and the residue recrystallized from IMS (300 ml) to give the desired product (22.1 g, 68% yield).

Stage 3

2'-Fluoro-4'-(4,4,5,5-tetramethyl-[1,3,2]dioxaborolan-2-yl)-biphenyl-4-carbonitrile (11 g, 34.1 mmol), 4-iodobromobenzene (9.7 g, 34.3 mmol), 1,4-dioxane (70 ml), water (35 ml) and potassium phosphate (24 g, 113 mmol) were ultrasonicated for 30 minutes. 1,1'-Bis(diphenylphosphino) ferrocenedichloropalladium II (0.5 g, 0.8 mmol) was added and the mixture heated at 30° C. for 20 minutes, 35° C. for 20 minutes then 40° C. for 80 minutes. The mixture was cooled. Water (100 ml) and DCM (300 ml) were added. The two layers were separated and the aqueous layer extracted with DCM (2×100 ml). The solvent from the organic layer was removed in vacuo. The residue was purified by vacuum flash chromatography on silica (60 g) eluting with toluene. The material was impure so was further purified by vacuum flash chromatography on silica (180 g) eluting with toluene to give the desired product (11.1 g, 93% yield).
Stage 4 mmol) was added dropwise over 10 minutes at 15° C.-20° C. The mixture was stirred for a further 2 hours at room temperature. Water (80 ml) and concentrated hydrochloric acid (20 ml) were added and the solvent removed in vacuo. The residue was extracted with DCM (500 and 2×100 ml)

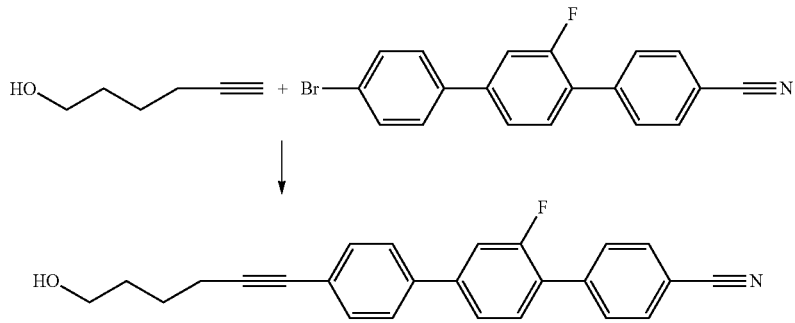

4"-Bromo-2'-fluoro-[1,1';4',1"]terphenyl-4-carbonitrile (8.6 g, 24.4 mmol), 4-pentyn-1-ol (2.6 g, 31.3 mmol), THF (130 ml) and diisopropylamine (13 ml, 93 mmol) were ultrasonicated for 30 minutes. Copper 1 iodide (130 mg, 0.67 mmol), bis(triphenylphosphine)palladium dichloride (0.26 g, 0.37 mmol) were added and the mixture was heated to 90° C. for 4.5 hours. The mixture was cooled. DCM (350 ml), water (50 ml) and concentrated hydrochloric acid (13 ml) were added. The two layers were separated and the aqueous layer extracted with DCM (2×50 ml). The solid was dissolved in DCM/THF 9:1 and purified by vacuum flash chromatography on silica (180 g) eluting with DCM/THF 9:1 to give the desired product (6.77 g, 78% yield).
Stage 5 the organic layer was dried over anhydrous sodium sulphate, filtered and the solvent from the filtrate removed in vacuo. The solid was dissolved in DCM (60 ml) and triethylamine (40 ml). The mixture was stirred at 40° C. for 2 hours then left overnight at room temperature. Water (100 ml) and concentrated hydrochloric acid (40 ml) were added and the two layers separated. The aqueous layer was extracted with DCM (2×50 ml). The combined organic layer was dried over anhydrous sodium sulphate, filtered and the solvent from the filtrate removed in vacuo. The residue was crystallised from acetonitrile (40 ml) to give the desired product (7.53 g, 81% yield).

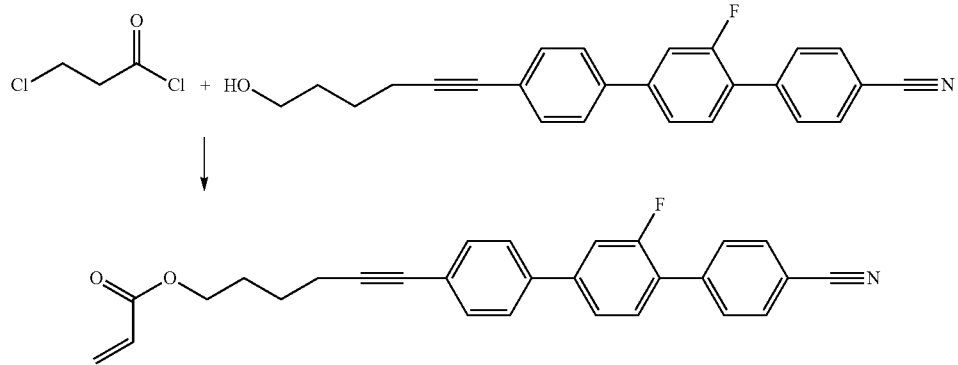

2'-Fluoro-4"-(6-hydroxy-hex-1-ynyl)-[1,1';4',1"]terphenyl-4-carbonitrile (8.1 g, 22.8 mmol), THF (400 ml), triethylamine (17 ml, 122 mmol) and DMAP (few crystals) were stirred at 15° C. 3-Chloropropionyl chloride (2.5 ml, 29

Examples 3-8

The following compounds were prepared in analogy to the synthesis described in Examples 1 and 2.

| No. | Structure | LC phase |
|---|---|---|
| RM3 | ![structure] | K 99.8 N 148 I |

| No. | Structure | LC phase |
|---|---|---|
| RM4 | 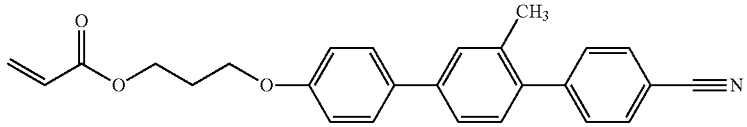 | K 144.9 I |
| RM5 | 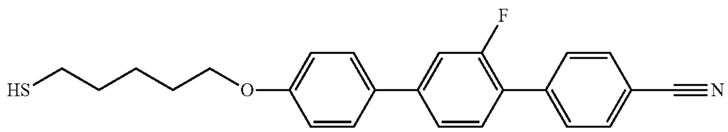 | K 97.2 N 209 I |
| RM6 | 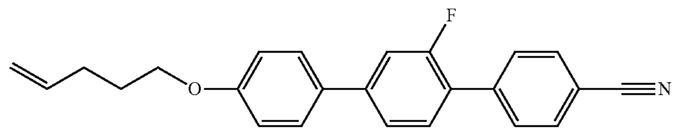 | K 88.5 N 217.3 I |
| RM7 | 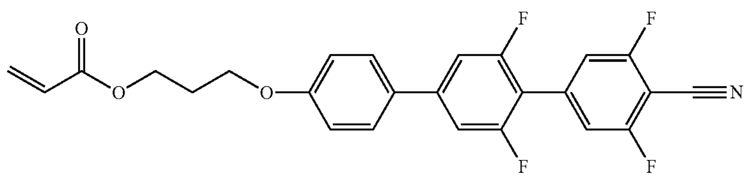 | K 160.5 I |
| RM8 | 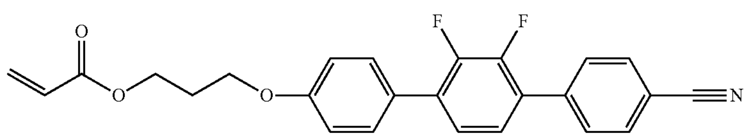 | K 148 N 177 I |

Comparison Example 1

Compound (C0) was prepared as described below.

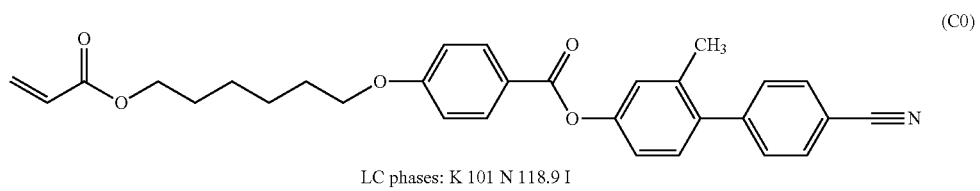 [SMILES: C=CC(=O)OCCCCCCOc1ccc(C(=O)Oc2ccc(-c3ccc(C#N)cc3)c(C)c2)cc1]

(C0)

LC phases: K 101 N 118.9 I

Stage 1

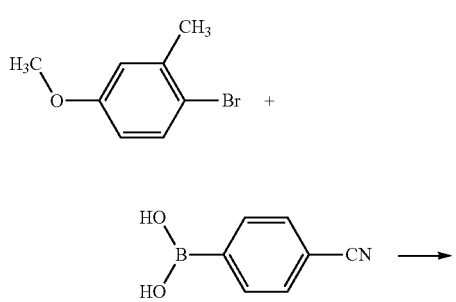

-continued

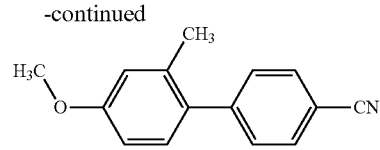

In the nitrogen atmosphere, a mixture of 2-bromo-5-methoxytoluene (30 g, 14 mmol), 4-cyanophenyl boronic acid (21.9 g, 14 mmol), sodium metaborohydrate octahydrate (61.7 g, 22 mmol), tetrahydrofuran (500 ml) and water (50 ml) were ultrasonicated for 30 minutes. Palladium(II) (triphenylphosphine)dichloride was then added and the mixture heated to 85° C. for 48 h. The mixture was cooled, water added and the two layers separated, further extraction was carried out using dichloromethane (due to poor solubility). The solvent from the organic layers were combined, dried with magnesium sulphate and concentrated in vacuo. The residue was purified by column chromatography eluting with petrol 40-60° C.:DCM from 4:1 to 3:1 ratio. The fractions containing the product were combined and the solvent removed in vacuo. The solid was recrystallised from acetonitrile to give the desired product 4'-methoxy-2'-methyl-biphenyl-4-carbonitrile (17.0 g, 51% yield).
Stage 2

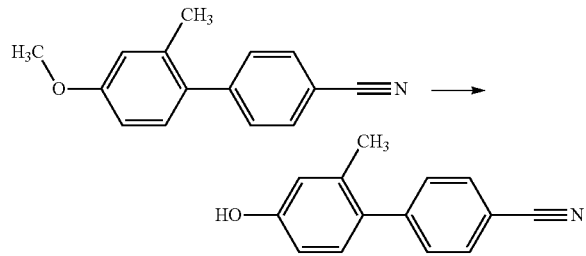

4'-Hydroxy-2'-methyl-biphenyl-4-carbonitrile (10 g, 44 mmol), aluminium chloride (7.97 g, 59 mmol) and anhydrous toluene (264 ml) were heated to reflux for 48 h under nitrogen atmosphere. Upon completion, the reaction mixture was allowed to cool to room temperature and then slowly poured into ice. Butanone was added and the two layers separated, the aqueous layer was further extracted with butanone. The organic layers were combined, dried over magnesium sulphate and concentrated in vacuo. The residue was purified by column chromatography eluting with petrol 40-60° C.:DCM from 2:1 to 1:2 ratio. The fractions containing the product were combined and the solvent removed in vacuo. The solid was recrystallised from acetonitrile to give the desired product 4'-hydroxy-2'-methyl-biphenyl-4-carbonitrile (6.60 g, 70% yield).
Stage 3

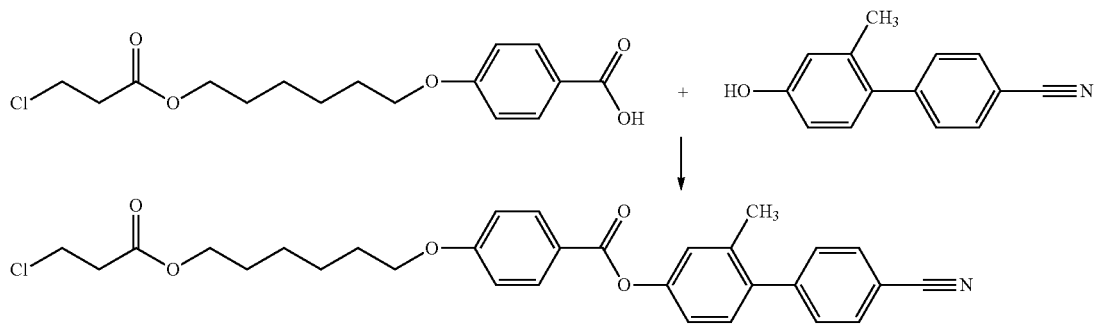

A mixture of 4-[6-(3-Chloro-propionyloxy)-hexyloxy]-benzoic acid (6.29 g, 19 mmol), dicloromethane (37.5 ml) and trifluoroacetic anhydride (2.66 ml) were stirred for 2 hour at 30° C. 4'-Hydroxy-2'-methyl-biphenyl-4-carbonitrile (4.00 g, 19 mmol) in DCM (37.5 ml) was stirred in a second flask, the premade mixed anhydride was then added to the alcohol and the reaction mixture stirred for 12 h at 30° C. The reaction was allowed to cool, water added to quench the reaction and extracted with DCM. The organic layers were combined, washed with sodium hydrogen carbonate solution, washed with water twice until pH=7. The organic material was dried over magnesium suphate and concentrated in vacuo. The residue was purified by column chromatography eluting with petrol 40-60° C.:DCM 1:2 ratio. The fractions containing the product were combined and the solvent removed in vacuo. The solid was recrystallised from acetonitrile to give the desired product 4-[6-(3-chloro-propionyloxy)-hexyloxy]-benzoic acid 4'-cyano-2-methyl-biphenyl-4-yl ester (5.35 g, 53.8% yield).
Stage 4

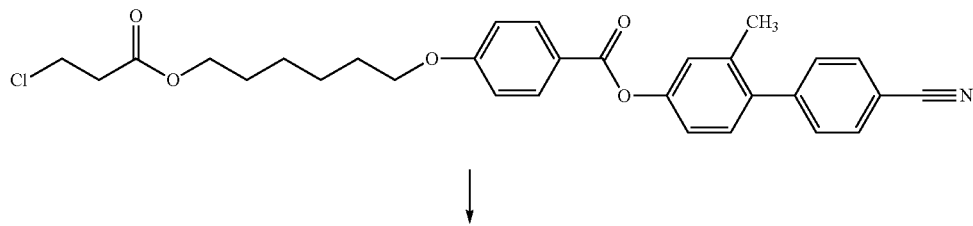

-continued

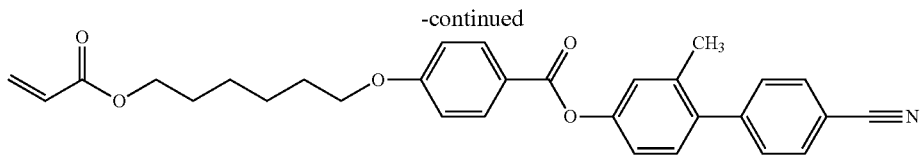

Triethylamine was added dropwise to a stirred solution of 4-[6-(3-Chloro-propionyloxy)-hexyloxy]-benzoic acid 4'-cyano-2-methyl-biphenyl-4-yl ester (6.0 g, 11 mmol) in DCM (100 ml) at room temperature (care exothermic). Upon complete addition, the reaction mixture was stirred at 35° C. for 12 h. The reaction mixture was allowed to cool, washed with water, dilute hydrochloric acid and again water. The combined organic layers were dried over sodium sulphate and concentrated in vacuo. The residue was purified by column chromatography eluting with petrol 40-60° C.:DCM 1:2 ratio. The fractions containing the product were combined, added irganox 1076 and the solvent removed in vacuo. The solid was recrystallised from acetonitrile to give the desired product 4-(6-acryloyloxy-hexyloxy)-benzoic acid 4'-cyano-2-methyl-biphenyl-4-yl ester (2.20 g, 39.4% yield).

The following compounds were prepared in analogy to the synthesis described in Comparison Example 1.

Where colour difference values $\Delta L^*$, $\Delta a^*$, and $\Delta b^*$ are calculated according to the following formulae:

$$\Delta L^* = L^* - L^*_t \qquad \Delta a^* = a^* - a^*_t \qquad \Delta b^* = b^* - b^*_t$$

Where $L^*$, $a^*$, $b^*$ are measured values of specimen and $L^*_t$, $a^*_t$, $b^*_t$ are values of target color and $L^*t=100$, $a^*t=0$ and $b^*t=0$ when comparing materials to a colourless reference (e.g white tile). Yellow index was measured using a Konica Minolta CR300 colour camera, in reflection mode. In this test an empty PI glass cell measured at a b value of 4.14 (for reference).

| No. | Structure | LC phase |
|---|---|---|
| C1 | 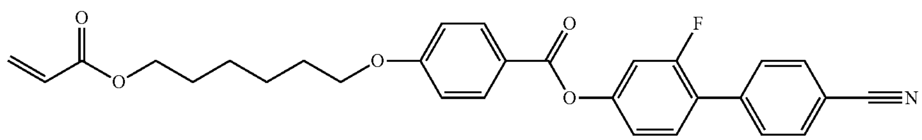 [SMILES: C=CC(=O)OCCCCCCOc1ccc(C(=O)Oc2ccc(-c3ccc(C#N)cc3)c(F)c2)cc1] | K 106.5 N Polymerises |
| C2 | 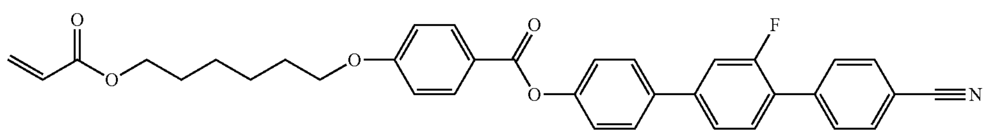 [SMILES: C=CC(=O)OCCCCCCOc1ccc(C(=O)Oc2ccc(-c3ccc(-c4ccc(C#N)cc4)c(F)c3)cc2)cc1] | K 140 N Polymerises |
| C3 | 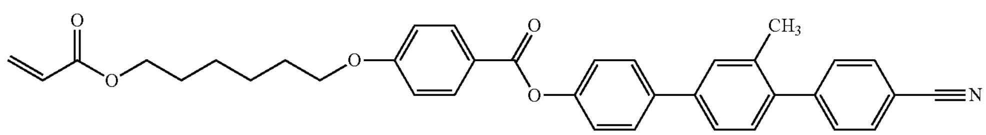 [SMILES: C=CC(=O)OCCCCCCOc1ccc(C(=O)Oc2ccc(-c3ccc(-c4ccc(C#N)cc4)c(C)c3)cc2)cc1] | K 142.7 N Polymerises |

Use Example 1

UV-Vis spectroscopy was used to measure compound yellowing by measuring the percentage transmission for each of the RM compounds across the visible range. This was done by dissolving 1 wt % of each RM in a solvent, usually DCM, and measuring the solutions percentage transmission on the Hitachi UV-Vis spectrometer, with air as a baseline. The solutions were then cured at a variety of different doses (0, 100, 500, 1000 and 3000 mJ) and the transmission measured again. Anhydrous dichloromethane was used to dissolve the singles, as it remains unaffected when exposed to UV light. By comparing these percentage transmissions it could be concluded which singles yellow and to what extent. $\Delta E(lab)$ was then calculated according to Equation 1 below, where total colour difference $\Delta E^*ab$ was also measured using the $L^*a^*b^*$ colour coordinates and defined by the Equation 1 below:

$$\Delta E^*_{ab} = \sqrt{(\Delta L^*)^2 + (\Delta a^*)^2 + (\Delta b^*)^2} \qquad (1)$$

Table 1 and FIG. 1 show the results of UV-light studies for compounds RM1-RM6 of the invention in comparison to compounds C1-C6 of prior art. In FIG. 1, the left column (for each individual compound) shows the $\Delta E(Lab)$ value before cure, and the right column shows the $\Delta E(Lab)$ value after cure.

It can be seen that compounds RM1, RM2, RM5 and RM6 show the least amount of change in yellowing when exposed to UV-light. In comparison, the compounds wherein the terphenyl core unit is interrupted by an ester functionality, like for example C1, show a significant increase in yellowing. Compound RM3 according to the invention also shows a slight increase in yellowing after cure, while compound RM4 surprisingly remained at similar values before and after cure. Thiolene compounds like RM5 show even smaller change to UV-light than the mono- and diacrylate compounds RM1-4.

TABLE 1

Comparison ΔE(lab) data of various RMs in anhydrous DCM

| Compound | LC Phase | ΔE(Lab) Before Cure | ΔE(Lab) After Cure | Change |
|---|---|---|---|---|
| RM1 | K 138.5 N 190 I | 0.2 | 0.353 | 0.113 |
| RM2 | K 122 Polymerise | 1.60 | 1.59 | −0.010 |
| RM3 | K 99.8 N 148 I | 1.14 | 1.76 | 0.623 |
| RM4 | K 143 N Polymerise | 0.42 | 0.20 | −0.215 |
| RM6 | K88.52 N 217.27 I | 0.11 | 0.11 | 0.005 |
| RM5 | K 97.16 N 209.02 I | 0.10 | 0.16 | 0.062 |

TABLE 1-continued

Comparison ΔE(lab) data of various RMs in anhydrous DCM

| Compound | LC Phase | ΔE(Lab) Before Cure | ΔE(Lab) After Cure | Change |
|---|---|---|---|---|
| C1 | K 106.5 N Polymerise | 0.64 | 2.28 | 1.639 |
| C4 | K 63.5 I | 0.82 | 4.42 | 3.60 |
| C5 | K 87.6 N 117.9 I | 0.45 | 2.56 | 2.12 |
| C6 | K 70.7 N 125.6 I | 0.53 | 3.05 | 2.53 |
| C7 | K 75.8 (N 53) I | 0.79 | 1.61 | 0.82 |

TABLE 2

Compound Structures:

| No. | Structure |
|---|---|
| RM1 | acrylate–O–(CH₂)₃–O–C₆H₄–C₆H₃(F)–C₆H₄–CN |
| RM2 | acrylate–O–(CH₂)₂–C≡C–C₆H₄–C₆H₃(F)–C₆H₄–CN |
| RM3 | acrylate–O–(CH₂)₆–O–C₆H₄–C₆H₃(F)–C₆H₄–CN |
| RM4 | acrylate–O–(CH₂)₃–O–C₆H₄–C₆H₃(CH₃)–C₆H₄–CN |
| RM5 | HS–(CH₂)₅–O–C₆H₄–C₆H₃(F)–C₆H₄–CN |
| RM6 | CH₂=CH–(CH₂)₃–O–C₆H₄–C₆H₃(F)–C₆H₄–CN |
| C1 | acrylate–O–(CH₂)₆–O–C₆H₄–COO–C₆H₃(F)–C₆H₄–CN |
| C4 | CH₂=CHCOO(CH₂)₆O–C₆H₄–COO–C₆H₄–CH₃ |

TABLE 2-continued

Compound Structures:

No. Structure

C5 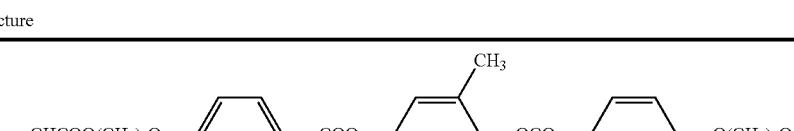

C6

C7

Use Example 2

RM mixtures were formulated as follows, which contain 20% of one of compounds RM1, RM2, RM3 or RM4 according to this invention, or one of the comparison compounds C0, C1, C2 or C3 as shown above.

For comparison purpose, an RM mixture ("host RMM") was formulated from compounds (1)-(5), Irgacure 651® and Irganox 1076®, but without containing any of compounds RM1, RM2, RM3, RM4, C0, C1, C2 or C3, and wherein the concentrations of compounds (1)-(5) were increased proportionally.

The RM mixtures were dissolved in dichloromethane (DCM) with 1% solid content. UV-Vis spectroscopy measurements were carried for the individual RM mixtures as described in Use Example 1. The details are summarised below:

Each RM single (1 wt % solid) is dissolved in a solvent, usually anhydrous DCM as it remains unaffected when exposed to UV light. The solutions percentage transmission are measured on the Hitachi UV-Vis spectrometer (UV visible3310 from 250 to 800 nm in 2 nm intervals) with air as a baseline. The solutions are then cured at a variety of different doses (0, 100, 500, 1000 and 3000 mJ) and the transmission measured again. The measurements of solu-

| Compound: | % Composition: |
|---|---|
| Compound (1) | 15.78 |
| Compound (2) | 19.73 |
| Compound (3) | 11.84 |
| Compound (4) | 23.68 |
| Compound (5) | 7.89 |
| RM1-RM4 or C0-C3 | 20.00 |
| Irgacure 651 ® | 1.00 |
| Irganox 1076 ® | 0.08 |
| Total | 100.00 |

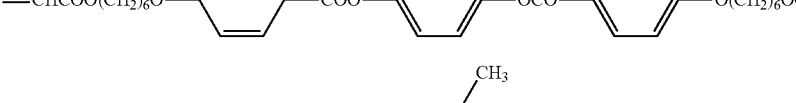

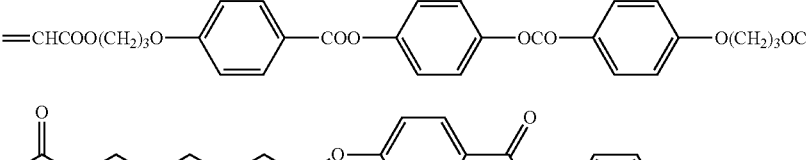

tions after 3000 mJ exposure are carried out using 50 mW/cm² power at 60 seconds duration with a Mercury Lamp. The ΔLab of each RM single are then calculated at 0 mJ and 3000 mJ doses (see Example 1).

Polymer films were prepared from each individual RM mixture as follows:

For the thick films b values, alignment and the birefringence (Δn) were measured by preparing RM singles, 20% in a host mixture RMM1134 (RMM1). The mixtures are flow filled into 20 μm cells at 2° C. below their TNI. The filled cells are then annealed for 2 minutes at 2° C. below the TNI, after which they are cooled to 20° C. using a circulator for 3 minutes. The films are cured using an Exfos lamp between 250-450 nm and 50 Mw/cm² power for 60 seconds. The b-values are then measured using Konica Minolta colour camera (as described in Example 1). The films are post baked at 100° C. for 5 minutes and the b-values measured again using the same method above (Example 1). The same films are used to measure the retardation, thickness and calculate birefringence (Δn).

The Δn of the films was calculated using the formula Δn=R/d, wherein
R=retardation as explained below
d=thickness as mentioned below
Δn values are given at λ=550 nm Retardation of these thin films was measured at 550 nm with ellipsometer. The thickness of the film was measured by making a scratch in a polymerized film and measuring the depth of the scratch with an Alpha step surface profileometer. Yellow index of the films was measured using a Konica Minolta CR300 colour camera, in reflection mode. In this test an empty PI glass cell measures at a b value of 4.14 (for reference). Films which have b values of ~4.14 indicate that it is completely transparent, whereas films with higher b values means that they are yellow in colour and thus the RM are unstable to UV light. i.e. the greater the b value the more yellow the film. The RM compounds below were added as a 20% composition to the RMM mixture.

The details are summarised below:

The thin films (order of 1 micron thick) birefringence (Δn) was measured by adding 0.6% FluroN562 or FC171 to the RMM mixture. Then a 25% solution of RMM was prepared in toluene, filtered through 0.2 μm PTFE and spin coated at 4000 rpm for 30 seconds. The filled cells are annealed at 10° C. below the TNI, cooled to 20° C. for 1 minute and purged with Nitrogen. The filled cells are then cured using Exfos lamp 250-450 nm, power 50 mW/cm2 for 60 seconds under nitrogen. The retardations are measured on the ellipsometer (checking first the films are not slayed). The films are scratched and the thickness measured on the surface profileometer.

The b-value and birefringence of the resulting RM mixtures are summarized in Table 3 below.

From Table 3, it can be seen that compound RM2 with a tolane group in the spacer shows slightly higher yellowing after cure with a b-value of 9.9 film after cure (see column 6) compared to RM1 and RM4 (see column 6). Compared thereto, compounds C1 and C3 show increased yellowing comparable to the host and the empty cell. Nevertheless, overall the compounds RM1 to RM4 according to the invention are better suitable for use as low yellowing singles, especially when comparing the ΔE(Lab) percentage transmission change in anhydrous DCM (see column 5). RM1 proved to be the best candidate as highly birefringent polymerisable component in RM mixtures, as it also shows low yellowing (see column 6), in comparison to compounds C0-C4 of prior art. The lower yellowing was observed for all RM1-RM4 in the singles percentage transmission ΔE(Lab) data compared to compounds C0-C4 of prior art.

TABLE 3

| | % T in DCM | | | | Film data (20%) | | | |
| | | | | | b-values | | | |
| | | ΔE(Lab) | | | Film | Film after | Δn | Δn |
| RM # | % T shift | Before Cure | After Cure | Change | after cure | post bake | (thick cell) | (thin film) |
| Host RMM | — | — | — | — | 5.29 | 4.8 | 0.157 | 0.160 |
| RM1 | 0.2 | 0.2 | 0.353 | 0.113 | 6.09 | 4.97 | 0.174 | 0.1956 |
| RM2 | 0 | 1.60 | 1.59 | −0.010 | 9.9 | 5.0 | 0.236 | — |
| RM3 | 2 | 1.14 | 1.76 | 0.623 | — | — | — | — |
| RM4 | 2 | 0.42 | 0.20 | −0.215 | 7.79 | — | 0.183 | — |
| C0 | 56 | 0.61 | 1.76 | 1.154 | 6.3 | 5 | 0.163 | 0.1751 |
| C1 | 76 | 0.64 | 2.28 | 1.639 | 6.96 | — | 0.195 | — |
| C2 | 58 | 0.85 | 3.71 | 2.859 | 6.37 | — | — | — |
| C3 | 84 | 0.37 | 5.59 | 5.221 | 7.33 | — | — | — |

The invention claimed is:
1. A compound of formula

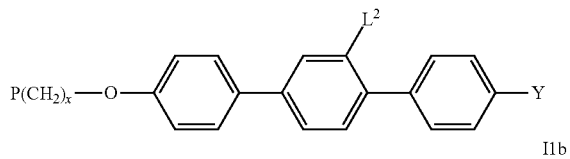

IIa

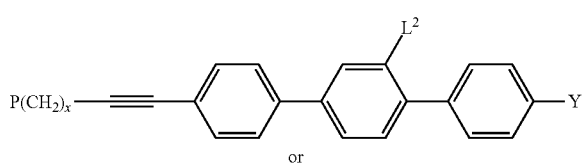

IIb or

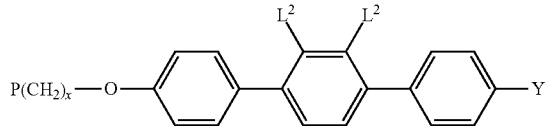

IIc wherein
P is a polymerizable group,
each L² is independently of each other P-Sp-, F, Cl, Br, I, —CN, —NO₂, —NCO, —NCS, —OCN, —SCN, —C(=O)NR⁰⁰R⁰⁰⁰, —C(=O)X⁰, —C(=O)OR⁰⁰, —C(=O)R⁰⁰, —NR⁰⁰R⁰⁰⁰, —OH, —SF₅, optionally substituted silyl, aryl or heteroaryl with 1 to 12, C atoms or straight chain or branched alkyl, alkoxy, alkylcarbonyl, alkoxycarbonyl, alkylcarbonyloxy or alkoxycarbonyloxy with 1 to 12 C atoms, wherein one or more H atoms are optionally replaced by F or Cl,
Sp is a spacer group,
R⁰⁰, R⁰⁰⁰ independently of each other denote H or alkyl with 1 to 12 C-atoms,
X⁰ is F or Cl,
Y is CN
and x is an integer 3 to 6.

2. The compound of claim 1, wherein P is selected from the group consisting of vinyloxy, acrylate, methacrylate, fluoroacrylate, chloroacrylate, oxetane and epoxide groups.

3. The compound of claim 1, wherein $L^2$ denote independently of each other F or $CH_3$.

4. A mixture comprising two or more reactive mesogens (RMs), at least one of which is a compound of formula according to claim 1.

5. The mixture according to claim 4, comprising one or more RMs having only one polymerizable functional group, and one or more RMs having two or more polymerizable functional groups.

6. A formulation comprising one or more compounds of formula according to claim 1, and further comprising one or more solvents and/or additives.

7. A polymer obtained by polymerizing a compound of formula or an RM mixture comprising a compound according to claim 1.

8. The polymer according to claim 7, wherein the RM mixture is aligned.

9. The polymer according to claim 7, wherein polymerization is conducted at a temperature where the RM mixture exhibits a liquid crystal phase.

10. An optical, electrooptical or electronic device or a component thereof, comprising an compound, RM mixture or polymer according to any of claims 1, 4, or 7.

11. The component of claim 10, which is selected from the group consisting of optical retardation films, polarizers, compensators, beam splitters, reflective films, alignment layers, colour filters, antistatic protection sheets, electromagnetic interference protection sheets, polarization controlled lenses, and IR reflection films.

12. The device of claim 10, which is selected from the group consisting of electrooptical displays, LC displays, autostereoscopic 3D displays, organic light emitting diodes (OLEDs), optical data storage devices and windows.

* * * * *